(12) United States Patent  
Barstis et al.

(10) Patent No.: US 9,354,181 B2  
(45) Date of Patent: May 31, 2016

(54) ANALYTICAL DEVICES FOR DETECTION OF LOW-QUALITY PHARMACEUTICALS

(75) Inventors: Toni Lee Owen Barstis, Niles, MI (US); Patrick Joseph Flynn, Granger, IN (US); Marya Lieberman, South Bend, IN (US)

(73) Assignees: Saint Mary's College, Notre Dame, IN (US); University of Notre Dame du Lac, Notre Dame, IN (US)

( * ) Notice: Subject to any disclaimer, the term of this patent is extended or adjusted under 35 U.S.C. 154(b) by 665 days.

(21) Appl. No.: 13/566,915

(22) Filed: Aug. 3, 2012

(65) Prior Publication Data

US 2013/0034908 A1 Feb. 7, 2013

Related U.S. Application Data

(60) Provisional application No. 61/515,235, filed on Aug. 4, 2011, provisional application No. 61/614,963, filed on Mar. 23, 2012.

(51) Int. Cl.
| | |
|---|---|
| *G01N 33/52* | (2006.01) |
| *G01N 21/78* | (2006.01) |
| *G01N 31/22* | (2006.01) |
| *G01N 21/84* | (2006.01) |

(52) U.S. Cl.  
CPC ............ *G01N 21/78* (2013.01); *G01N 21/8483* (2013.01); *G01N 31/22* (2013.01); *G01N 2021/8488* (2013.01); *Y10T 436/11* (2015.01); *Y10T 436/19* (2015.01)

(58) Field of Classification Search  
CPC ............ B01J 2219/00547; B01J 2219/00549; G01N 2035/00782; G01N 35/00871; G01N 35/00; G01N 2500/00; G01N 21/6428; G01N 30/88; G01N 33/56966; G01N 30/74; G01N 2021/6417; G01N 21/25; G01N 21/643  
USPC .................. 436/43, 124, 164; 422/430, 82.05  
See application file for complete search history.

(56) References Cited

U.S. PATENT DOCUMENTS

| | | | | |
|---|---|---|---|---|
| 5,843,691 | A | * 12/1998 | Douglas et al. | ................. 435/14 |
| 6,136,549 | A | 10/2000 | Feistel | ........................... 435/7.1 |

(Continued)

FOREIGN PATENT DOCUMENTS

WO    WO 2007/077444 A1    7/2007

OTHER PUBLICATIONS

Martinez et al. "Diagnostics for the Developing World: Microfluidic Paper-Based Analytical Devices", Anal. Chem., 2010, v. 82, pp. 3-10.*

Ress et al. "Automatic acquisition of fiducial markers and alignment of images in tilt series for electron tomography", J. Electron Microscopy, 1999, v. 48, No. 3, pp. 277-287.*

(Continued)

*Primary Examiner* — Yelena G Gakh  
(74) *Attorney, Agent, or Firm* — Winston & Strawn LLP

(57) ABSTRACT

An analytical device, in particular, a paper analytical device (PAD), for detection of at least two chemical components indicative of a low quality pharmaceutical product is provided. The analytical device can include a porous, hydrophilic medium, at least two assay regions associated with the porous, hydrophilic medium, at least one assay reagent or precursor thereof in the assay regions, and at least one optically readable information zone.

20 Claims, 10 Drawing Sheets

(56) References Cited

U.S. PATENT DOCUMENTS

| | | | |
|---|---|---|---|
| 6,770,487 B2 | 8/2004 | Crosby | 436/518 |
| 6,847,451 B2 | 1/2005 | Pugh | 356/436 |
| 7,344,081 B2 | 3/2008 | Tseng | 235/462.13 |
| 7,885,444 B2 | 2/2011 | Wang | 382/128 |
| 8,655,009 B2 * | 2/2014 | Chen | G01N 21/274 382/100 |
| 2008/0012083 A1 | 1/2008 | Gilton | 257/432 |
| 2011/0111517 A1 | 5/2011 | Siegel | 436/164 |
| 2011/0189786 A1 | 8/2011 | Reches et al. | 436/164 |

OTHER PUBLICATIONS

Lu, Y. et al. Short Communication, Rapid Prototyping of Paper-Based Microfluidics With Wax for Low-Cost, Portable Bioassay, Electrophoresis, vol. 30, 1-4 (2009).

Carrilho, E. et al., Understanding Wax Printing: A Simple Micropatterning Process for Paper-Based Microfluidics, Anal. Chem., vol. 81, pp. 7091-7095 (2009).

Green M. et al., "Determination of Oseltamivir Quality by Colorimetric and Liquid Chromatographic Methods", Emerging Infectious Diseases, vol. 14, No. 4 , pp. 552-556 (2008).

* cited by examiner

ANALYTICAL DEVICES FOR DETECTION OF LOW-QUALITY PHARMACEUTICALS

CROSS-REFERENCE TO RELATED APPLICATION

This application claims the benefit of provisional application No. 61/515,235 filed Aug. 4, 2011, and provisional application No. 61/614,963 filed Mar. 23, 2012. The entire content of each prior filed application is expressly incorporated herein by reference thereto.

FIELD OF THE INVENTION

The invention relates to user-friendly analytical devices, in particular, Paper Analytical Devices (PADs), for detection of at least two chemical components indicative of a low quality pharmaceutical product, and method of use thereof.

BACKGROUND OF THE INVENTION

User-friendly analytical devices such as Paper Analytical Devices (PADs) are known in the art as convenient and inexpensive means for assaying chemicals. As these devices contain all necessary reagents and do not require power, they are easy to operate in a field setting. U.S. Pat. No. 6,136,549 discloses systems for conducting spectrophotometric analysis which includes a chromatographic medium, such as an assay test strip, that is designed to be contacted with a test solution having activated magnetic particles. U.S. Pat. No. 6,770,487 discloses "dip stick" style paper-based diagnostic test devices, in which identifying information and the test result are machine-readable. U.S. Pat. No. 6,847,451 discloses apparatuses for determining the concentration of an analyte in a physiological sample, which include at least one light source, a detector array, means for determining whether a sufficient amount of sample is present on each of the plurality of different areas, and means for determining the concentration of the analyte based on the reflected light detected from those areas determined to have sufficient sample. U.S. Pat. No. 7,344,081 discloses a method of automatically detecting a test result of a probe zone of a test strip comprising capturing an image of a one-dimensional bar code and an image of at least one test strip from a scanning object, and determining a setting value for the at least one test strip based, at least in part, on said captured image of said bar code. U.S. Pat. No. 7,885,444 discloses a method for determining a response of each probe zone on a test strip by selecting an average pixel value of each section of reference white respectively adjacent to the image of a target line to serve as a reference for determining a color response of the target line. US patent application publication no. 2008/0012083 discloses an analytical system-on-a-chip that can be used as an analytical imaging device, for example, for detecting the presence of a chemical compound, which may also include software that can detect and analyze the output signals of the device. US patent application publication no. 2011/0189786 discloses a method of detecting the presence or absence of an analyte in a fluid sample includes applying the sample to an inlet zone of a diagnostic system that includes a hydrophilic cotton loading thread to serve as a capillary to deliver a solute to a reagent testing zone, and detect color change of reagent analyte interaction. US patent application publication no. 2011/0111517 discloses a paper-based microfluidic assay device comprising a porous, hydrophilic substrate; a fluid-impermeable barrier defining a boundary of an assay region and a boundary of a main channel region, the main channel region fluidically connected to the assay region; and a strip of conductive material disposed on the porous, hydrophilic substrate for detecting the concentration/flow of analyte. pSiFlow Technology Inc. provides a mobile testing and process management web infrastructure built around its Calibrated Color Match (CCM) image processing technology, which enables digital reading of color-based test strips using any mobile phone with a camera.

The World Health Organization (WHO) reports that many medications for sale in underdeveloped countries are of low quality, which either contain low concentrations of active ingredients that are not sufficient to treat the underlying condition, or contain substitute active ingredients that may have adverse effects on some patients, or have no active ingredients at all; or even contain toxic ingredients. Although the prevalence of such medications is difficult to measure, both the WHO and US Food and Drug Administration (FDA) estimate that 10-30% of all drugs in the developing world are low quality drugs. A consumer taking a low quality pharmaceutical product may die or experience other adverse medical effects from the underlying condition or from contaminants in the pharmaceutical product. The failure of treatment may be mistaken for resistant strains of the disease requiring much more rigorous treatment that can itself endanger the patient. Also, low quality medications that fail to cure the underlying condition may speed up development of actual resistance in pathogens.

Multiple factors contribute to the prevalence of low quality pharmaceutical products in developing countries. First of all, manufacturing and selling low quality pharmaceutical products are both easy and hugely lucrative, and low quality products can enter the supply chain at many points. Moreover, buyers and consumers cannot assess identity or quality of pharmaceutical products. Furthermore, manufacturing low quality pharmaceutical products is not a serious crime in many countries, and there is a low risk of detection from official agencies and organizations. Finally, the time, expertise, and expense required for testing pharmaceutical products is a particular barrier to effective post-market surveillance of pharmaceuticals in developing countries.

Some medical conditions arise not from a pathogen, but from a deficiency in an essential nutrient. For example, widespread iodine deficiency is a problem in many underdeveloped countries that is associated with developmental impairment in children. Fortification of table salt with potassium iodate or potassium iodide is a common route to address this problem. However, production and distribution methods for iodized table salt in many developing countries yield inadequate or inconsistent levels of iodine. Unfortunately, the time and expense of testing for iodized table salt deters manufacturers, distributors, and end-users from testing iodized table salt to determine iodine concentrations. Thus, a low-cost method of testing iodized table salt at the production facility or in the field is needed to determine whether the salt is adequately fortified with iodine within therapeutic concentrations recommended by the WHO.

Thus, there exist long-felt needs for a low-cost, easy-to-use, reliable, minimalistic chemical means of detecting low quality pharmaceutical products and nutritional supplements such as iodized salt. These quality problems are also present for veterinary medications and nutritional supplements for animals. The present invention addresses these needs by providing an inexpensive, user-friendly, consistent analytical device capable of detecting various low quality pharmaceutical products and measuring levels of iodine in iodized salt.

SUMMARY OF THE INVENTION

The present invention provides an easy-to-use, inexpensive analytical device, typically a Paper Analytical Device (PAD), for detection or analysis of at least two chemical components in a dosage formulation indicative of a low quality pharmaceutical product or nutritional supplement. The analytical device typically comprises a porous, hydrophilic medium; at least two assay regions associated with the porous, hydrophilic medium; at least one assay reagent or precursor thereof deposited in the at least two assay regions; and at least one optically readable information zone which after activation of the device provides color information necessary for identification of the device and analysis or detection of the at least two chemical components. Typically, the porous, hydrophilic medium is paper, such as Ahlstrom 319 blotting paper. Preferably, the least one optically readable information zone comprises alignment references/marks for transforming and/or correcting a captured image of the analytical device such as the analytical device to facilitate analysis and processing of the color information to more accurately detect the at least two chemical components.

In one embodiment, the alignment references include a plurality of fiducial markers for orienting the captured image, and the device further includes at least one of an identification tag such as a two-dimensional barcode, and a color calibration zone.

Typically, a hydrophobic barrier or an air gap defines multiple assay regions with multiple assay reagents or precursors thereof arranged in a defined pattern to facilitate contact with the chemical components to be tested.

In one embodiment, the analytical device of the invention also comprises user compliance regions that include a timer region.

Typically, the chemical components to be detected by the analytical device of the invention include an active ingredient and an excipient. The active ingredient to be detected generally includes an anti-malarial, antibiotic, anti-parasitic, cox-inhibitor, analgesic, antipyretic or anti-viral compound. The excipient to be detected generally includes binders, fillers, tablet coatings, and other non-active ingredients. In some embodiments, the chemical compounds to be detected by the paper analytical device of the invention include degradation products that may be present in low-quality pharmaceutical products, and/or substitute pharmaceutical or excipient ingredients that are sometimes present in counterfeit formulations. In some embodiments, the chemical compounds to be detected include micronutrients.

The invention also provides a method for detection of at least two chemical components indicative of a low quality pharmaceutical product. The method typically comprises providing an analytical device of the invention; disposing the pharmaceutical product to be analyzed into the assay region of the device; activating the device in a manner such that the assay reagents contact the product to be analyzed in the assay regions to provide color information; and analyzing the color information to detect the presence or absence of the at least two chemical components. Processing of the color information provided by the device can determine whether an inappropriate combination of active ingredient and excipient is present, whether substitute ingredients or degradation products are present, whether the active pharmaceutical ingredient is present in an amount that is significantly below the expected amount, or whether the ratio of two active pharmaceutical ingredients or that of an active pharmaceutical ingredient and an excipient is outside the expected range—all characteristics that are indicative of a low quality pharmaceutical product or nutritional supplement.

In one embodiment of the method of the invention, the pharmaceutical product to be analyzed is disposed upon the assay regions by swiping the pharmaceutical product across the device or by applying a dilution containing the pharmaceutical product onto the device. Disposing the pharmaceutical product into the assay region and activating the device cause a color change that can be analyzed to detect the presence or absence of the chemical components in the pharmaceutical product.

In a preferred embodiment of the method of the invention, the analytical device further includes a color calibration zone and the method further comprises automating the color analyzing by capturing an image of the device using a camera device; and providing image analysis software capable of recognizing and quantifying a color change within the assay regions of the device that is shown in the captured image. The paper analytical device used in the method of the invention typically includes a plurality of fiducial markers for orienting the captured image so that the image software can correct or transform the captured image based on these fiducial marks, thereby aligning the captured image with stored images in the database, read test results from pre-specified regions in transformed image, and classify the test results. Preferably, the method of the invention further comprises providing the image analysis software on the camera device for processing the captured image in situ, or on a network server to process the captured image by sending the image to the network server that performs the analysis and transmitting detection results back to the camera device.

In a preferred embodiment, the method of the invention further comprises repeating the detection for a plurality of pharmaceutical products; and compiling a database of the captured images of the analytical devices, which includes time stamping and geo-tagging of the captured images.

The analytical device used in the method of the invention typically includes a plurality of fiducial markers for orienting the captured image so that the image software can correct or transform the captured image based on these fiducial marks, thereby aligning the captured image with stored images in the database, read test results from pre-specified regions in transformed image, and classify the test results. Preferably, the method of the invention further comprises providing the image analysis software on the camera device for processing the captured image in situ, or on a network server to process the captured image by sending the image to the network server that performs the analysis and transmitting detection results back to the camera device.

Typically, the chemical components to be detected by the method of the invention include an active ingredient and an excipient, and (1) the presence of one of the chemical components determines that the pharmaceutical product contains an insufficient amount of active ingredient; (2) the absence of one of the chemical components determines that the pharmaceutical product does not contain an appropriate active ingredient; (3) the absence of one of the chemical components determines that the pharmaceutical product does not contain an appropriate excipient; or (4) the presence of one of the chemical components determines that the pharmaceutical product contains an inappropriate excipient. The active ingredient generally includes an anti-malarial, antibiotic, anti-parasitic, cox-inhibitor, analgesic, antipyretic or anti-viral compound, and the color information determines whether an inappropriate combination of active ingredient and excipient is present, indicative of a low quality pharmaceutical product.

The invention also provides a method for identifying geographical areas or points in time that low quality pharmaceutical products are being provided. This method typically comprises collecting images of color information as described hereinabove and compiling a database of the captured images of the analytical devices, including time stamping and geo-tagging of the captured images, followed by processing the database to identify locations or times that a plurality of low quality pharmaceutical products are being provided. This method may further comprises collecting an image from analysis of a further pharmaceutical product, and comparing results to the images in the database to identify locations where similar low quality pharmaceutical products are being provided.

Another embodiment of the invention is a kit for detection of at least two chemical components indicative of a low quality pharmaceutical product. Typically, the kit comprises an analytical device, typically a PAD, as disclosed herein; a solvent sufficient to prepare the sample and/or saturate the device; and instructions for detecting the presence or absence of the at least two chemical components indicative of a low quality pharmaceutical product. Preferably, the solvent is present in an amount sufficient to dilute the pharmaceutical product to be analyzed to an analyzable concentration. Typically, the solvent is water, ethanol, or methanol, and preferably, deionized water.

The invention also provides an analytical device, typically a PAD, for analyzing the quality of a pharmaceutical or food product, such as an iodized table salt. Such a device typically comprises a porous, hydrophilic medium, typically paper; at least two hydrophilic regions associated with the porous, hydrophilic medium; at least one assay reagent or precursor thereof in each of the at least two assay regions, wherein the at least one assay reagent or precursor is capable of identifying a component of the pharmaceutical or food product, and is present at different concentrations in each of the at least two assay regions to facilitate quantitative analysis of said component; at least one optically readable information zone which after activation of the device provides color information necessary for quantitative analysis of said component; and a color calibration zone. Preferably, the least one optically readable information zone comprises alignment references/markers for transforming or correcting a captured image of the analytical device such as the PAD to facilitate analysis and processing of the color information to more accurately detect the quantity of said component in the pharmaceutical or food product. In a preferred embodiment, the pharmaceutical or food product is an iodized salt, and the component to be analyzed is iodate ($IO_3^-$) and/or iodide (I), and/or diethylcarbamizine citrate (DEC).

The invention also provides a method for analyzing the quality of an iodized salt which comprises providing an analytical device, typically a PAD as disclosed herein; activating the analytical device for receipt of an iodized salt; disposing the iodized salt to be analyzed into the assay regions of the device in a manner such that it contacts the assay reagents in the assay regions to provide color information; capturing an image of the device using a camera device; providing image analysis software capable of recognizing and quantifying a color change within the assay regions of the device that is shown in the captured image; and determining the quantity of iodine in the iodized salt.

Another embodiment of the invention is a kit for analyzing the quality of an iodized salt comprising an analytical device, typically a PAD as disclosed herein, and instructions for using the kit to detect the quantity of $KIO_3$ in the iodized salt using the kit, or a link to retrieve the instructions from a website.

BRIEF DESCRIPTION OF THE DRAWINGS

Further features of the invention, its nature and various advantages will be more apparent from the following detailed description, taken in conjunction with the accompanying drawings in which like reference characters refer to like parts throughout and in which.

DETAIL DESCRIPTION OF THE PREFERRED EMBODIMENTS

Figure 1:
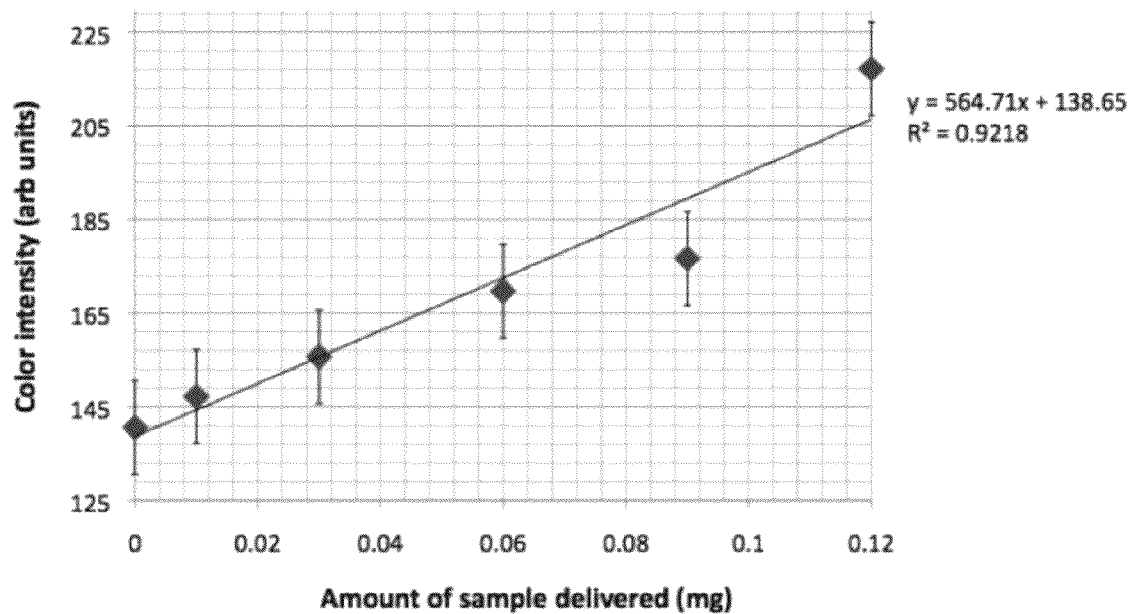
FIG. 1 shows the correlation between extent of color change and amount of acetaminophen on an acetaminophen PAD according to one embodiment.

As used herein, "paper analytical device" (or "PAD") refers to a composition based on a porous hydrophilic material (such as paper) and comprising areas of hydrophobic barriers which define hydrophilic assay areas. The hydrophilic assay areas may include test reagents.

As used herein, "low quality pharmaceutical product" refers to a pharmaceutical product purported to be a genuine product for treating a disease or disorder but containing low concentrations of active ingredients that are not sufficient to treat said disease or disorder, a pharmaceutical product containing substitute active ingredients that may have undesired side effects compared to the stated drug, a pharmaceutical product containing active ingredients that have undergone degradation, or a pharmaceutical product having no active ingredients at all. In addition, this term includes pharmaceutical products that contain ingredients that should not be present in a genuine pharmaceutical product of the stated type including ingredients that may be toxic.

As used herein, "active agent" refers to a chemical capable of being detected by an analytical device as disclosed herein, such as a PAD. The active agent may include pharmaceutical active ingredients, excipients or anticipated degradation products within a pharmaceutical formulation.

As used herein, a "camera device" refers to a device that contains a camera component. Exemplary camera devices are various types of digital cameras and scanners as well as mobile devices such as cell phones, smartphones or similar devices. When digital cameras are used, the images will be uploaded to a computer or other electronic device that is capable of transmitting the pictures to another location. Of course, when a picture or image is taken from a mobile phone, the phone already generally has the ability to forward the image, e.g., as a text message or as part of an e-mail.

The present invention provides an easy-to-use, inexpensive analytical device, such as a PAD, for detection of specific chemicals and/or chemical groups in an active ingredient, which is particularly capable of detecting various low quality pharmaceutical products and iodized salt. One advantage of the present invention is that more than active pharmaceutical ingredients can be analyzed with the same device, which is especially useful in analyzing a combination drug. Moreover, in addition to verification of an appropriate active pharmaceutical ingredient that should be present, it is also possible to screen for binders and fillers that should be present in the stated formulation, e.g., starch as a binder in acetaminophen tablets; and additionally, to screen for a multitude of likely substitute drugs, e.g., an antipyretic in place of expensive anti-malarial drugs, ampicillin in place of erythromycin, and binders or fillers such as gypsum or lactose in place of an active pharmaceutical.

Porous Hydrophilic Substrate

Typically, the analytical device of the invention comprises a porous, hydrophilic medium, preferably a paper such as a fast chromatography paper or an absorbant blotting paper. A suitable porous hydrophilic medium includes one that has a fast flow rate via capillary action, has enough absorption capacity to hold adequate amounts of reagent; has durability and stability such that it does not fall apart or fall over when wet; and is compatible with at least one of the methods used to fashion assay regions. Characteristics which should be considered when designing an analytical device of the invention, such as a PAD, include solvent flow-rate through the unfabricated substrate, printability, density, thickness, pH, basis weight, solvent flow-rate through fabricated substrate, compatibility with fabrication methods, pore size, and porosity. Preferred characteristics include high solvent flow-rate through unfabricated substrate and a comparable solvent flow-rate through fabricated substrate, a substrate that is printable, flexible, but sturdy enough to resist tearing when scratched with a pip (or other formulation), a medium thickness around about 0.4-0.6 mm, pH relatively close to neutral, a medium density and weight, resistance to deterioration caused by fabrication methods and materials, and a large pore size. Examples of suitable materials for an analytical device of the invention, such as a PAD, include, but are not limited to nitrocellulose acetate, chromatography paper, cellulose acetate, cellulosic paper, filter paper, tissue paper, writing paper, paper towel, cloth, and porous polymer film. In one embodiment, the substrate for a PAD is Whatman 3 mM Chr chromatography paper, Ahlstrom 205, Ahlstrom 222, Ahlstrom 226, Ahlstrom 319, or Whatman No. 1 filter paper. In one preferred embodiment, Ahlstrom 319 filter paper is used.

The basis weight ($g/m^2$) of the PAD can range from about 50 $g/m^2$ to about 400 $g/m^2$. Specific preferable basis weights include about 90, 176, 187, 192, and 307 $g/m^2$. Thickness of the PAD can range from about 1.0 mm to about 0.10 mm thick. Specific preferable thickness include 0.18, 0.47, 0.48, 0.69, and 0.83 mm. The PAD can have a pH ranging from about 6.0 to about 8.0. Specific preferable pHs can include 5.81, 5.99, 6.25, 6.31, and 7.09. Pore size can range from about 10.0 micrometers to about 30 micrometers. Specific preferable pore sizes include about 11.0, 19.0, and 22.0 micrometers. The most preferable basis weight is about 192.0 $g/m^2$, the most preferable thickness is about 0.48 mm, the most preferable pH is about 5.99, and the most preferable pore size is about 19.0 micrometers.

Fabrication of the PAD and Assay Regions Thereupon

The final dimension of the PAD can have a length "L", width "W" and height or depth "H" that can vary, depending on the number and size of assay regions and information zones needed on the PAD. For example, in one embodiment, the PAD can be 1.75 inches long, by 3 inches wide. In another embodiment, the PAD may be 5 inches long by 3 inches wide. The height or depth is determined by the specific paper substrate and fabrication method used. In one embodiment an inert backing material is required, which will increase the PAD depth; in another embodiment, laminated or layered structures are produced which again increase the PAD depth. In some embodiments, the PAD may include a region or flap that is designed to be folded over by the user during or after use.

Several assay regions are defined on the analytical device of the invention, either by affixing individual strips or other shapes cut from paper onto an inert backing material, or by patterning a piece of paper with a hydrophobic barrier substantially permeating the thickness of the paper medium to define the boundaries of the desired assay regions. The hydrophilic assay regions or reaction areas with the boundaries defined by the hydrophobic area can be in any suitable size or shape. The precise dimensions of the assay regions are determined by the type of reaction to be performed within each assay region, or for optimizing viewing results. Suitable shapes for reaction areas include rectangular lanes, circles (or "spots"), squares, triangles, etc. Reaction areas can comprise multiple shapes. For example, a rectangular lane may culminate with a circle. Alternatively, two overlapping circles can form a "peanut" reaction area. The diameter of each circle (including the peanuts) can range from about 1.5 cm to about 0.3 cm. Preferably the circles are about 1.0 cm in diameter. The peanuts can range from about 3 cm in vertical length to about 1.0 cm in vertical length. Preferably, the peanuts can be about 1.8 cm in vertical length. The length of rectangular lanes can range from about 1 cm to the full length of the PAD, and the width can range from about 0.1 cm to the full width of the PAD.

In one preferred embodiment, twelve rectangular lanes are placed on the PAD, each lane being 7 cm in length and 0.3 cm in width. The area of the reaction area must be sufficient to contain the necessary amounts of embedded reagents to interact with the chemicals to be detected, and the lane dimensions must be large enough that the color produced in the chemical reactions can be clearly distinguished by the camera device.

The assay regions of the PAD can be produced in a number of ways that are known to one skilled in the art. For example, photolithography of a resist such as SU-8 can be used to produce hydrophobic regions within the hydrophilic paper medium according to the procedures laid out in US patent application publication nos. 20110111517 A1, which is herein incorporated in its entirety. Alternately, the PAD can be fabricated using wax printing according to the procedures laid out in Lu, Y.; Shi, W.; Jiang, L.; Qin, J.; Lin, B. *Electrophoresis* 2009, 30, p. 1497-1500 and Carrilho, E.; Martinez, A. W.; Whitesides, G. M. *Anal. Chem.* 2009, 81, p. 7091-7095, which are herein incorporated in their entireties. In a preferred embodiment, an HP Color Qube printer is used to deposit wax ink, preferably black, in the desired regions of Ahlstrom 319 paper according to a template laid out in a computer program such as Adobe Illustrator; alternatively, the template may be stored and printed as an image file such as a PDF. The preferred paper type is too thick for wax deposition on one side of the paper to form the necessary continuous hydrophobic barrier, so wax ink must be printed on both sides of the paper, after which the paper is heated to 70-120° C. (preferably 100° C.) to allow the wax to melt through the paper and form a continuous hydrophobic barrier surrounding the desired assay region. For prototyping, a wax crayon can be applied heavily around the regions desired on both the front and back of the paper, after which the paper is heated to 70-120° C. (preferably 100° C.) to allow the wax to melt through the paper and forth a continuous hydrophobic barrier surrounding the desired assay region.

The "cut and paste" method requires the lanes to be cut from the hydrophilic paper medium and adhered to a relatively strong backing, mylar plastic for example, using an adhesive. This method does not require the application of a hydrophobic agent in order to define the hydrophilic reaction areas. As a result, the chance of bleed-over of hydrophobic agent into the lanes is eliminated. The lanes can be cut using any precise cutter, such as an exacto-knife or craft cutter.

Reagents And Reagent Deposition

The analytical device also contains at least one assay reagent in each of the assay regions. In one embodiment, a hydrophobic barrier defines independent isolated assay regions of various shapes and at least one of the assay regions includes a reagent or precursor thereof that is capable of identifying a component that should not be present in the pharmaceutical product.

Various reagents or regent forming precursors can be optionally loaded into the reaction areas. The reagents or precursors can be loaded into the reaction area individually by hand, or via an automated process. The regents are loaded as liquid solutions or suspensions, and allowed to dry prior to use of the analytical device such as a PAD. Examples of reagent materials suitable for use in the analytical device of invention such as a PAD include, but are not limited to, Folin-Ciocalteu, potassium hexacyanoferrate(II) trihydrate, iodine-potassium iodide reagent, universal indicator, ferric chloride, triiodide, triiodide-starch complex, soluble starch; cationic, anionic, and neutral pH indicators; barium chloride, sodium rhodizonate, potassium hexacyanoferrate(II), NaOH, tosic acid, potassium carbonate, citric acid, copper sulfate, sodium tetraphenylborate, cobalt thiocyanate, ammonium molybdate, nitroaniline, 1,2-napthaquinone-4-sulfonate, dimethylglyoxime, and paradimethylaminobenzaldehyde. These reagents may be deposited from aqueous solution or from organic solution. For wax printed PADs, acetonitrile is the preferred organic solvent because the wax barriers are not affected by the acetonitrile. Surprisingly, many colorimetric reagents plateau at particular concentrations so that adding additional reagents will not enhance color results. Thus, the upper limit on the amount of reagents added is more or less determined by the PAD's loading capacity. The volume of the reagent loaded onto the PAD can range from about 2 to about 100 microliters, or from about 10 to about 50 microliters, or preferably from about 20 to about 30 microliters.

Reagents may be deposited on the surface of the analytical device in many ways that will be familiar to those skilled in the art, including but not limited to the use of: microcapillary pipettes and droppers, single- or multi-channel automatic pipetting devices, rods that can capture a droplet of solution or "frog" type depositors that perform this function with multiple rods simultaneously, dipping or spraying equipment, or solution deposition robots. In one preferred embodiment, the reagents are manually deposited using an automatic pipette. In another preferred embodiment, the reagents are deposited using a Biomek 96-well-plate replicating robot.

General Method of Use

The invention also provides a method for detecting the presence or absence of a chemical and/or a chemical functional group in a composition, or for quantifying the amount of at least one chemical in a composition, or for comparing the amounts of two chemicals present in the composition. This method comprises providing a paper analytical device of the invention; disposing the composition into the assay region in a manner such that it contacts the assay reagent or reagents in the assay region; and analyzing the assay region to detect the presence or absence of the chemical and/or the chemical functional group in the composition or to detect the amount of the targeted chemical or chemicals present in the assay region or to compare the amounts of two chemicals present in the composition.

Compositions Suitable for Analysis

The chemicals to be detected can be in any suitable formulation, including tablets, pills, solids, or powders. Other suitable formulations include liquids, such as suspensions, syrups, or solutions of medications. In some instances, a solid formulation can be used directly with the PAD, by swiping or rubbing the formulation onto the PAD at a specific location(s). In other instances, a solid formulation must be diluted into a liquid solution or suspension in order to be used with the specific PAD. Liquid formulations may be added directly to the PAD, or may be further diluted and then added to the PAD. In some instances, a formulation may be used both directly, and also as a dilution on the same PAD.

The PADs can be used to detect low quality human and animal pharmaceutical products, including classes of treating agents such as anti-malarials (artemether, lumifantrine), beta lactam antibiotics (ampicillin, amoxicillin), cox-inhibitors, anti-parasitic drugs (albendazole, mebendazole, ivermectin), antipyretics (aspirin, acetaminophen) phosphodiesterase inhibitors (sildenafil citrate), and anti-virals (ostamilvir phosphate). They can also be used to analyze foodstuffs that have been supplemented or fortified with micronutrients (iodine, iron, zinc, vitamin C) or with medications (diethylcarbamazine citrate). However, other classes of active agents are also contemplated, such as NSAIDs (ibuprofen), analgesics (lidocine), HMG-CoA reductase inhibitors (statins), ace-inhibitors (quinapril), macrolide antibiotics (erythromycin), anti-anxiety medications (alprazolam), bi-polar disorder and schizophrenia medications (olanzapine), anemia medications (epoetin alfa), and anti-retrovirals (abacavir), etc. Specific PADs and their application are disclosed herein.

Deposition of the Composition to be Analyzed on the Pad and Activation of the Pad Tests In one embodiment, the solid composition is disposed within the assay region by swiping the composition across the surface of the paper analytical device. For example, a drug tablet may be broken in half and rubbed on the surface of the paper in the assay regions, or a rough surface such as a piece of wire or plastic mesh or sandpaper may be used to assist in forming powdered material on the assay regions. Alternatively, a solid formulation may be crushed or ground to powder, or a capsule containing powdered material may be opened, and the powder may be spread on the assay region using a paddle or spatula. Such deposition of solid material may be carried out with the aid of an assisting device, such as a plastic mesh or plate pierced with holes in regions that correspond to the locations of the assay regions. In order to deposit a controlled amount of the composition to be analyzed, a straight-edge may be drawn across the top surface of the assisting device to pack the composition within the holes of the assisting device, after which the assisting device is lifted from the PAD. The composition may be disposed within the assay region by placing a solution or suspension containing the composition drop-wise onto the desired region of the paper analytical device. Alternatively, the composition may be disposed within the assay region by dipping part of the PAD into the solution or suspension of the composition and allowing the composition to move into the assay region with the resulting capillary flow.

In the preferred embodiment, the reagents in the assay regions are activated by the addition of a solvent, preferably water although in some embodiments methanol, acetonitrile, or other organic solvents may be used. The solvent may simply be dropped onto an assay region, in one embodiment by addition to the assay regions of drops of a solvent containing a solution or suspension of the composition to be analyzed. Alternatively, the solvent may be applied by placing part of the PAD in contact with a porous material such as blotting paper that is wetted with the solvent. Alternatively, the solvent may be added by dipping part of the PAD directly into the solvent; in the preferred embodiment of this application method, the solvent is allowed to contact a part of the assay region and then fill the assay region by capillary action.

General Method of Analysis of the Test Results

Once the composition has been applied to the assay regions, the disposing of the solvent into the assay regions typically causes a colorimetric change in each region that can be analyzed to detect the presence/absence of the chemical and/or the chemical functional group in the composition, to quantify the amount of the targeted chemical, or to compare the amounts of two chemicals present in the composition.

The hydrophobic regions can also define control regions within the hydrophilic paper medium. For example, a timer region may be included in order to alert the user when the test has completed. The timer region may comprise a color-generating reaction in which one component travels up the lane with the solvent flow and creates a color when it encounters another component at the top of the lane, or it may comprise other timing mechanisms such as delay of the solvent flow by a deposited reagent such as sugars, surfactants, or polymers. Additionally, the PAD may include positive or negative control regions. A negative control may be included in order to verify that the PAD has not become contaminated during storage or use or that the solvent used to develop the colors does not interfere with a color generating reaction. A positive control may be included to show that the reagents in a test lane are still viable, or it may be used as a standard for the image analysis software as disclosed hereinbelow. The PAD may also contain assay regions whose only function is to demonstrate that the user has complied with instructions for correct use of the PADs, or assay regions whose function is to demonstrate that the PAD is an authentic device and not a counterfeit.

Information Identification Zone

The paper analytical device contains at least one electronically readable information zone which provides information necessary for determining the outcome of the test performed on the PAD based on images obtained by a camera device. The information zone typically includes appropriate information that is electrically readable per se or after being photographed, or otherwise imaged electronically. Such information may include an identification tag such as a two-dimensional bar code (e.g., a QR code), color standards, and/or fiducial or alignment marks.

Each PAD can be imprinted with a two-dimensional barcode such as a Quick Response (QR) barcode that contains the type and serial number of the PAD so that a PAD test can be uniquely identified and the necessary color processing steps to perform the test can be automatically determined, which provides a simple and inexpensive way to uniquely identify the PAD, in addition to providing pertinent information for perspective distortion correction and subsequent color analysis. Depending on the application, other information can also be encoded in the two-dimensional code image. A key task of the image analysis software is the perspective correction or transformation of distorted images, which transforms an image captured at an unknown standoff and optical axis position to a canonical coordinate system in which regions to be analyzed for subsequent color characterization are expressed. The origin and basis vectors for this coordinate system can be automatically calculated from the position of "finder marks" or fiducial marks on the QR code. In some embodiments, each PAD may also contain one or more additional fiducial markers such as "finder squares" or rectifiers to eliminate angle and 3D distortions of the PAD's photographed image. The identification zone can be placed anywhere on the PAD. Preferably, the identification zone can be printed on the PAD prior to application of hydrophobic regions and the identification zone is located on an upper corner of the PAD.

Color Calibration Zone

In analyzing a PAD, the color content of specific regions of the PAD will be analyzed to automatically determine the test result. This removes human subjectivity in color interpretation. However, PAD images may be captured under different ambient lighting conditions and their global effect on PAD color distributions must be suppressed. Thus, it is important to perform color calibration using the color calibration zone on the PAD, which consists of different colored sub-regions, including a white region and a black region. Image analysis software can be used to compare the extracted colors in the PAD image's color calibration zone to known values to identify the specific color correction methods needed. One such method is white balancing, in which the overall brightness of the image is adjusted to force the white square in the PAD image to have a pure white color value. The calibration zone can be in any suitable shape, including rectangles, squares, circles, or triangles. The sub-regions can be in any suitable shape, including rectangles, squares, circles or triangles. Preferably, the color calibration zone is a rectangle region and the sub-regions are different colored squares. The color calibration zone can be printed onto the PAD prior to or after application of hydrophobic regions. The calibration zone can be placed anywhere on the PAD. Preferably, the calibration zone is printed on the PAD prior to application of hydrophobic regions and is located on an upper corner of the PAD.

In the preferred embodiment, the PAD of the invention comprises one information zone having a color calibration zone, another information zone having multiple fiducial marks, and yet another information zone comprising a QR code or other identification tag.

The method further comprises providing a camera device, capturing an image of the PAD that has reacted with the composition using the camera device, and providing an image analysis software capable of using information provided by the information zone and the image of the test result in order to identify and quantify a colorimetric change within the assay region of the paper analytical device shown in the captured image. In the preferred embodiment of the method of the invention, the capture image contains a two-dimensional bar code such as a QR code and one or more fiducial markers. The image software identifies the QR code region, separates the image of the PAD's assay regions from background present in the picture, scales, rotates, and performs geometrical transformations on the captured PAD image based on the QR code and the one or more fiducial markers, aligns the PAD assay regions with stored images in the database, reads test results from pre-specified locations in the stored assay regions, and classifies the test results. The method of the invention further comprises compiling a database of the captured images of the paper analytical devices and the computed test outcomes, wherein the two-dimensional barcode is a QR code that allows for automated identification of a specific PAD including the PAD-type, serial number and fabrication date.

In one embodiment, the image analysis software is provided on the camera device for processing the captured image in situ. Alternatively, the image analysis software may be provided on a network server such that the captured image is processed by sending the picture to the network server that performs the analysis and transmits the results back to the camera device.

Controls

The hydrophobic regions can also define control regions within the hydrophilic paper medium. For example, a timer region may be included in order to alert the user when the test has completed. The time region may comprise a colorimetric indicator. Additionally, the PAD may include positive or negative control regions. A negative control may be included in order to verify the purity of the reaction solvent. A positive control may be included in order to verify the presence (or absence) of the chemical to be detected. The control substrates, if any, may be included in the paper medium at the time the other colorimetric reagents are added to the paper medium. The PAD may also contain hydrophilic regions for titrations and/or reverse titrations, as well as user compliance lanes for improving the accuracy of the quantitative analysis of the chemicals.

Kits

The PADs may be packaged in kits providing a user with all of the materials necessary for using the PAD. For example, the kit may contain a solvent (such as deionized water or ethanol), a plastic micropipette, weighing paper, and a cotton swab. Instructions may be provided as a paper insert within the kit, or may be printed on the outside of the kit container. The PADS comprising test reagents may be subjected to degradation due to temperature, light, or moisture which may affect the accuracy of the tests performed. As a result, the PADs may be individually packaged and sealed in light- and moisture-resistant packets. Additionally, the packets may be packaged with a desiccant in order to maintain a specific moisture level, and remove excess moisture. Another embodiment of the invention is a kit for detecting the presence/absence of a chemical and/or a chemical functional group in a composition, quantifying a chemical in a composition, or measuring the relative amounts of two materials present in a composition. Typically, the kit includes a PAD as disclosed herein; a solvent sufficient to saturate the paper assay device; and instructions for detecting the presence/absence of a chemical and/or a chemical functional group in a composition, quantifying a chemical in a composition, or measuring the relative amounts of two materials present in a composition. Preferably, the solvent is one that is sufficient to dissolve or suspend the composition containing the chemical and/or the chemical functional group to be analyzed. Typically, the kit contains a dish to hold the solvent and a spatula swab, or pipette for applying the composition onto the PAD.

EXAMPLES

Example 1

Paper Analytical Device for Analyzing Acetaminophen

Previously attempts were made to identify low quality acetaminophen tablets utilizing near-infrared spectroscopy, which is an expensive, time-consuming process. These products are known under the trade name Panadol or TYLENOL®.

The acetaminophen PAD contains tests that are adapted to the analysis of acetaminophen tablets. In particular, it is imperative to identify acetaminophen, the active ingredient. The structure of acetaminophen is shown below:

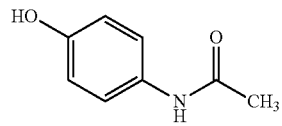

Acetaminophen structure

Figure 2:
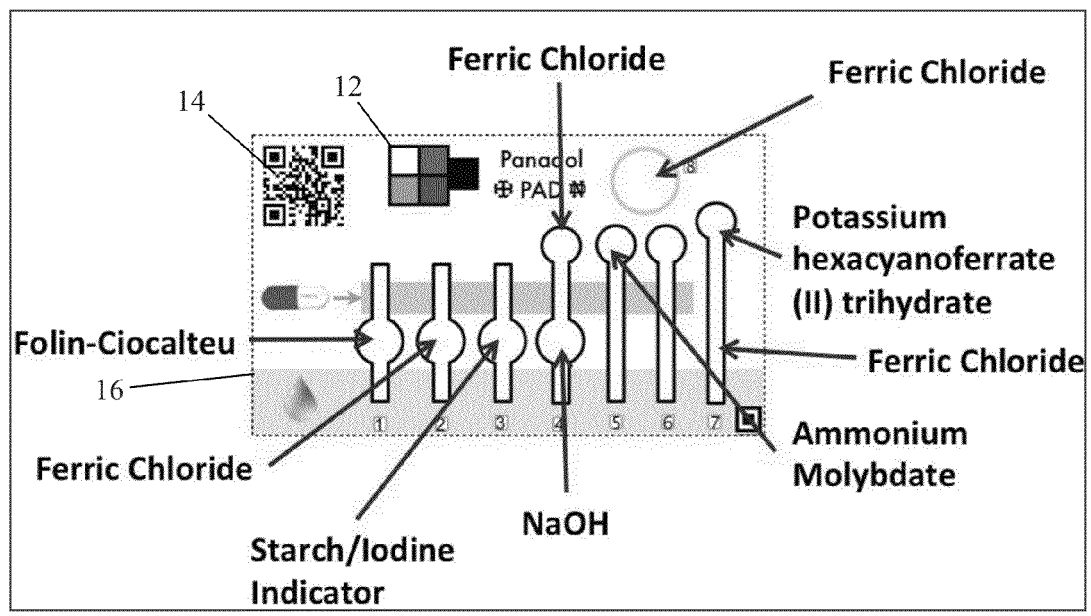
FIG. 2 depicts an acetaminophen PAD according to one embodiment.

FIG. 2 shows one embodiment of an acetaminophen PAD. The acetaminophen PAD comprises a color calibration zone 12, an identification zone 14, reaction areas (lanes 1-6, circle 8) as well as a timer region (lane 7). The lanes are generally rectangular in shape and include one or more circular areas that include reagent or precursor chemicals ("reagent areas"). The lanes are spaced horizontally but extend vertically on the PAD. A horizontal swipe line in the form of a band or zone that is present upon the PAD to indicate a deposition area where the pharmaceutical is to be disposed on the medium. This deposition area intersects each of the lanes in an area that is in a rectangular portion of the lane either above or below the reagent areas. The swipe line is shown extending from just prior to the lane 1 to just past the lane 6. The beginning of the swipe line is identified in FIG. 2 by the picture of a pill and arrow to indicate where the solid pill should be swiped so that chemicals from the pill will be present in a portion of each lane that is contacted by the pill.

A solvent contact zone 16 is present in a lower portion of the PAD. This zone 16 extends past the lower end of each lane below the reagent areas. The solvent contact zone 16 indicates how far the PAD needs to be placed into or contacted by a source of water. To assist in identifying the solvent contact zone, which for this PAD will use water as the solvent, a picture of a water droplet is shown on the left side of the solvent contact zone 16. When the solvent contact zone 16 of PAD receives water, part of the water is provided in the lower portion of each lane. The water therein then moves upwards through the lane by capillary action through each reagent area where the water contacts and dissolves or otherwise transports some of the reagent through the lane. Lanes 1-3 have reagent areas located between the solvent zone and swipe line while lane 4 has one reagent area located below the swipe line and a second reagent area located above the swipe line. Lanes 5-7 have reagent areas located above the swipe line. The capillary action of the water passing through the reagent areas in lanes 1-4 carries at least some of the reagent with it to the swipe line for reaction with chemicals deposited by the swiping of the pill across the lanes. Table 1 herein provides: an identification of the reagents embedded in the circular area(s) of each lane, the amounts embedded, the chemicals to be detected, the color change expected with a positive reaction, and the minimum amount of the chemical or active agent necessary in order to result in a positive reaction. The following is a description of the various regions of the PAD, their content and how they are used to analyze a particular sample of pharmaceutical product that is supposed to be genuine.

It is important to note that the reagents on the acetaminophen PAD test for ingredients that are commonly found in counterfeit pharmaceuticals of all varieties, not just acetaminophen. Moreover, acetaminophen itself is often a counterfeit ingredient in fake anti-malarials and antibiotics. For this reason, these reactions form the basis of a generic excipient PAD that can be used as an initial screening tool for any medicine.

Lane 1—Detecting Acetaminophen or Vitamin C

The Folin-Ciocalteu reagent contains a mixture of phosphomolybdate and phosphotungstate. Upon reaction with phenols, the substance changes from a light green to a dark green/blue color, which absorbs at 765 nm. The Folin-Ciocalteu indicator changes color in the presence of acetaminophen from a yellowish to greenish color. Vitamin C was found to produce a dark blue in the presence of Folin-Ciocalteu. The most distinct color change was observed when 20 uL of 2N Folin-Ciocalteu reagent is used.

ing an orange precipitate (ferric carbonate). The most distinct color change was observed when 20 uL of 7.39E-2M iron(III) chloride was used.

Lane 3—Detecting Starch, Vitamin C

An iodine test was developed to detect starch, which is often found in legitimate acetaminophen pills. The iodine

TABLE 1

| Lane or Circle | Reagent (uL) | Detects | Color | Limit of Detection for a positive reaction |
|---|---|---|---|---|
| 1 | Folin-Ciocalteu (20 uL) | Acetaminophen and Vitamin C | Acetaminophen yellow to greenish color Vitamin C yellow to dark blue | Acetaminophen 0.1 mg Vitamin C 0.1 mg |
| 2 | Ferric Chloride (20 uL) | Acetaminophen, Carbonates, and Salicylic Acid | Acetaminophen yellow to green-brown color Carbonates yellow to orange Salicylic acid yellow to a dark brown/black | Acetaminophen 1.9 mg Carbonates 0.5 mg Salicyclic Acid 0.5 mg |
| 3 | Iodine Indicator (40 uL) | Starch and Vitamin C | Starch brown to black Vitamin C brown to colorless | Starch 0.4 mg Vitamin C (N/A) |
| 4 | Ferric Chloride (5 uL) NaOH (10 uL) | Acetaminophen, Aspirin, and Salicylic Acid | Acetaminophen yellow to purple Aspirin yellow to purple Salicylic acid yellow to dark purple | Acetaminophen 0.3 mg Aspirin 0.5 mg Salicylic acid 0.9 mg |
| 5 | Ammonium Molybdate (10 uL) | Phosphate | blue to green | (N/A) |
| 7 | Ferric chloride (10 uL) Potassium hexacyanoferrate(II) trihydrate (2 uL) | Timer | no color to blue | (N/A) |
| 8 | Ferric Chloride (20 uL) | Acetaminophen, Carbonates, and Salicylic Acid | Acetaminophen yellow to green-brown color Carbonates yellow to orange Salicylic acid yellow to a dark brown/black | Acetaminophen 1.9 mg Carbonates 0.5 mg Salicyclic Acid 0.5 mg |

Lane 2, Circle 8—Detecting Acetaminophen, Salicylic Acid, or Carbonates

Additional qualitative tests may be included to detect acetaminophen. Lane 2 and circle 8 contain ferric chloride as the reagent. Lane 2 is a qualitative test, while circle 8 is quantitative. The ferric chloride test is a common qualitative test for organic derivatives. Although the unstable complex ion that shows the color change has not been isolated, it is known for its reactivity with phenols. The ferric chloride indicator changes color in the presence of acetaminophen from a yellowish to "mucus green-brown" color. A positive reaction with ferric chloride also produces a color gradient which can aid in determining concentrations for quantification of active ingredients. The detection of salicylic acid is achieved through its reaction with ferric chloride to produce a brown/black colored complex. The carbonate detection occurs through reaction with ferric chloride as well, producmolecule locates itself inside of the amylose ring of the starch molecule and forms a black colored complex indicating a positive result for starch. This test provides the PAD with an alternate method to verify the authenticity of a pill. Acetaminophen pills require the presence of cornstarch in their original recipe; therefore, a negative test indicates a low quality product.

Ascorbic acid/Vitamin C is often found as a filler in low quality acetaminophen products. In order to detect Vitamin C, it is necessary to adapt the known titration of ascorbic acid. Iodine is a powerful oxidant and Vitamin C is an anti-oxidant. As a result, the combination of the two produces a colorimetric change rapidly. The mixture of Vitamin C and starch/iodine mixture produces a quenching of any color to white. This occurs because the iodine molecule delocalizes itself from the amylose ring to react with Vitamin C, thus quenching the original brown color or the black color typically seen with starch. The most distinct color change was observed when equal parts of potassium iodide, iodine, and tosic acid were used.

Lane 4—Detecting Acetaminophen, Aspirin, and Salicylic Acid

Sodium hydroxide, a strong base, will hydrolyze aspirin, salicylic acid, or acetaminophen, yielding an anion that will complex with iron (III) to form a purple colored complex, according the proposed mechanisms below (left for aspirin and salicylic acid and right for acetaminophen). Note that the iron complex is purple, but a green color can appear with excess iron (III). For salicylic acid, the resulting complex is the same, yet a darker purple color.

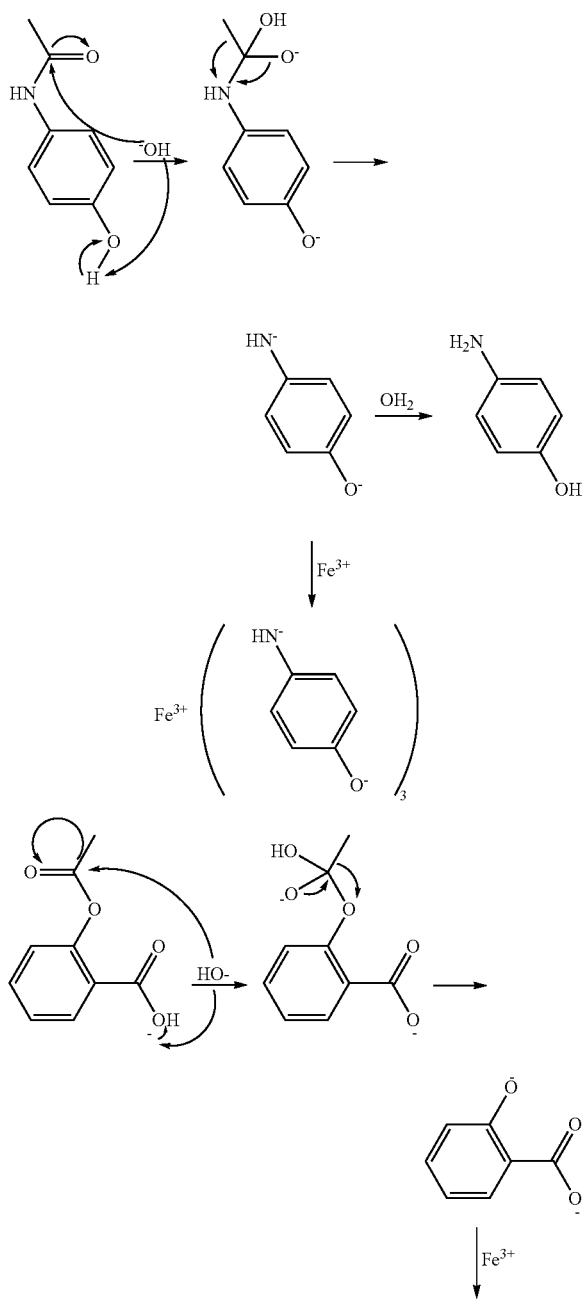

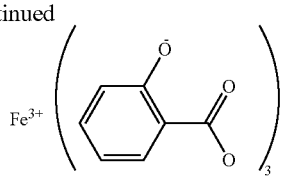

Aspirin, also known as acetyl salicylic acid, is a common filler in low quality pharmaceutical products including low quality acetaminophen products. Salicylic acid is a degraded product of aspirin and thus is itself a common filler in low quality acetaminophen drugs. The most distinct color change was observed when 10 uL of 3M sodium hydroxide solution and 5 uL of 7.39E-2M iron(III) chloride was used.

Lane 5—Detecting Phosphate

Phosphates are found in gypsum ($CaSO_4.2H_2O$), a fake filler commonly found in low quality acetaminophen drugs. The chemical indicator ammonium molybdate can sometimes detect the presence of phosphates by undergoing a chemical reaction that produces a yellow colored complex. The molybdate indicator dries blue, so the presence of phosphates and the accompanying yellow complex produce a green color in the lane of the PAD. The most distinct color change occurred when 8 mg of ammonium molybdate was dissolved in 100 mL distilled $H_2O$, followed by an addition of 4 mL sulfuric acid.

Lane 7—Timer

Prussian blue is formed when ferric chloride and potassium hexacyanoferrate(II) trihydrate are combined. This reaction is used as a timer to indicate that adequate time has elapsed for all reactions on the PAD to occur completely. This confirms that the test has been properly run when imaged and forwarded for inclusion in the database.

Circle 8—Quantification of Acetaminophen

Circle 8 contains ferric chloride, the same reagent found in lane 2. According to the method of the invention, the pill of interest is dissolved in 15 mL of ethanol, and two drops of this solution are placed in circle 8. Because the pill is dissolved in a set volume of solution, circle 8 can determine how much acetaminophen is present. The yellow circle turns brown in the presence of acetaminophen, and a direct correlation between extent of color change and amount of acetaminophen has been shown. FIG. 1 shows this correlation; intensities were determined using the java-based image processing program Image J. The most distinct color change was observed when 20 uL of 7.39E-2M iron(III) chloride was used.

Large-Scale Validation of Acetaminophen PAD

In spring 2012, a series of field tests were completed in order to analytically validate the acetaminophen PAD and determine the reliability of the chemical reactions. Test participants were instructed to analyze a pill sample (with known ingredients, prepared by researchers) using a acetaminophen PAD, and send an image to the researchers' database. Most users were previously unfamiliar with PADs and PAD usage and ranged in age from 11-90. A total of 561 tests were completed, yielding 460 analyzable images to be studied by researchers (attrition due to technical difficulties and improper documentation). Table 1.1 below shows the rates of success with which the PAD detected various chemical samples. Accurate detection is defined by whether or not the expected color changes occurred based on the reactions described above. The results show that not all tests had satisfactory detection, particularly the tests for aspirin and phosphates (seen as monopotassium phosphate in Table 1.1). For this reason, research is being conducted to improve those chemical detection methods.

TABLE 1.1

| Sample Contents | Percentage of Accurate Detection | Sample Size |
|---|---|---|
| Acetaminophen (500 mg) + Starch | 84.1 | 138 |
| Acetaminophen (300 mg) + Starch | 78.8 | 33 |
| Acetaminophen (100 mg) + Starch | 78.0 | 41 |
| Vitamin C + Starch | 100.0 | 32 |
| Aspirin + Starch | 36.0 | 24 |
| Monopotassium Phosphate Starch | 40.9 | 22 |
| Acetaminophen + Sodium Bicarbonate | 78.8 | 32 |
| Acetaminophen + Calcium sulfate | 57.7 | 26 |
| Salicylic acid + Talc | 100.0 | 48 |
| Calcium Carbonate | 73.8 | 42 |

Despite the imperfect detection of many samples, the acetaminophen PADs overall were able to distinguish real drug products from low quality products with reasonable accuracy. A "real" sample is one which contains both acetaminophen and starch, and nothing else. Therefore, lack of one of these ingredients flags a pill as suspicious, as does the presence of any additional contaminants. The PAD results were analyzed to determine percentages of true positives, true negatives, false positives, and false negatives. The area of greatest concern is false positives, because this is when the PAD says a pill is of acceptable quality, but it is actually substandard; this percentage should be very low. Table 1.2 displays how true/false positives/negatives were defined, and Table 1.3 shows the percentages determined from analysis of field test results.

TABLE 1.2

| | What's actually in pill: | |
|---|---|---|
| What PAD said | Real Product | Substandard Product |
| Real | True + | False + |
| Low quality | False − | True − |

TABLE 1.3

| | What's actually in pill: | |
|---|---|---|
| What PAD said | Real Product | Substandard Product |
| Real | 30.7% | 3.03% |
| Low quality | 6.28% | 60.0% |

As Table 1.3 shows, the false positive rate is 3.03%. This leaves room for improvement, but a good rule of thumb is that the false positive rate should be less than or equal to the actual prevalence of fake pills. The lowest end of the WHO estimate for the prevalence of low quality products rests at 10%. Therefore, these results show that the acetaminophen PAD is accurate enough for use in the field as a drug screening tool for acetaminophen pills.

Example 2

Paper Analytical Device for Analyzing TAMIFLU®

One of the most prevalent anti-viral medications is TAMIFLU® (TAMIFLU® is a registered trademark of Hoffmann-LaRoche Inc.), a neuraminidase inhibitor that fights both influenza types A and B. Tamiflu® contains the active ingredient oseltamivir phosphate. The six to eight months synthesis time of oseltamivir phosphate, in conjunction with the increasing global demand for Tamiflu®, has led to a Tamiflu® shortage in recent years. This, in turn, has made the international market particularly vulnerable to low quality Tamiflu® products, which, unlike other low quality pharmaceutical products, always lack the active ingredient completely and thus, is never underdosed. Tragically, untreated influenza leaves infected individuals extremely susceptible to secondary infections that, in turn, can lead to death.

The structure of oseltamivir phosphate is shown below:

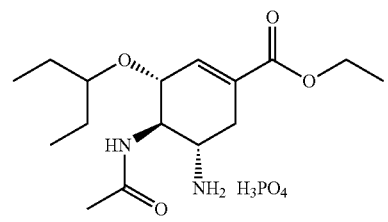

Oseltamivir phosphate structure

Figure 3:
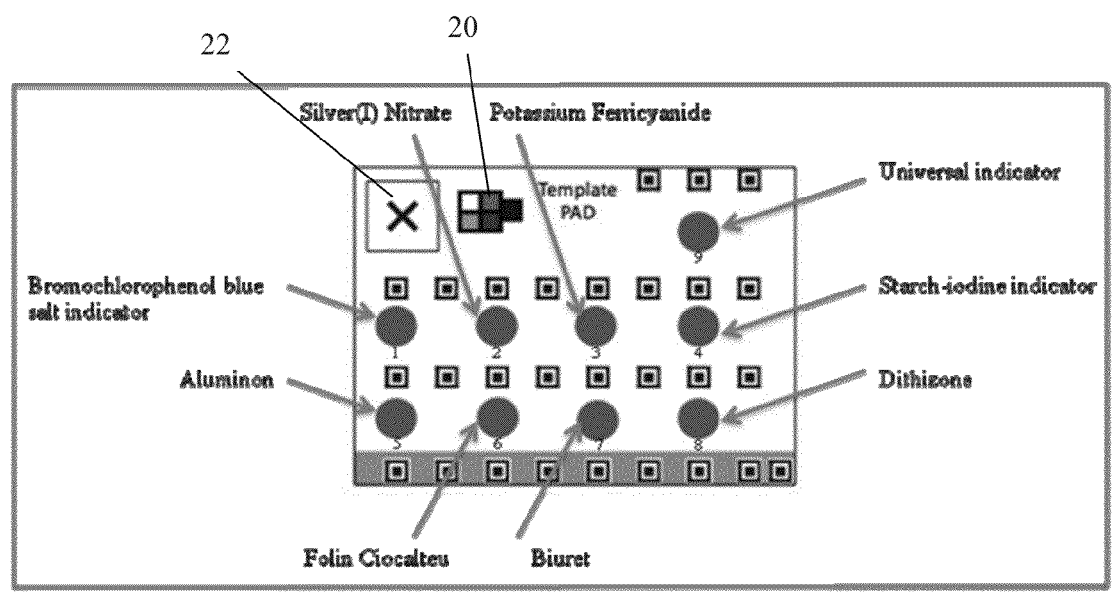
FIG. 3 depicts a TAMIFLU® PAD according to one embodiment.

FIG. 3 shows one embodiment of a Tamiflu® PAD. The Tamiflu® PAD comprises a color calibration zone (20), an identification zone (22), reaction areas (circles 1-9). Table 2 herein shows the location of the embedded reagents, the amounts embedded, the chemicals to be detected, the color change expected with a positive reaction, and the reasoning that reagent was included in the Tamiflu® PAD. The following is a description of the various regions of the PAD, including the associated chemistry.

To conduct testing, a pill is diluted in a water container with a fixed quantity of water, ideally 8 mL, and two drops of the solution are applied in all of the spots bordered in black.

TABLE 2

| Circle | Reagent (uL) | Detects | Color | Reason |
|---|---|---|---|---|
| 1 | Bromochlorophenol blue salt indicator (10 uL) | Oseltamivir phosphate | blue to a characteristic blue pattern | Bromochlorophenol blue salt indicator is an anionic dye (acidic) that forms a complex with the cationic oseltamivir (basic drug). This complex will confirm the presence of oseltamivir, the active ingredient of Tamiflu ®. |

TABLE 2-continued

| Circle | Reagent (uL) | Detects | Color | Reason |
|---|---|---|---|---|
| 2 | Silver(I) Nitrate (10 uL) | Phosphates | gray to yellow | Phosphate is present in genuine Tamiflu ®. An additional benefit of this test is that chloride ions (found in common salt, a commonly substituted filler in fake pharmaceuticals) can also be identified as a white precipitate. |
| 3 | Potassium Ferricyanide (10 uL) | Amines | blue to yellow or green, depending on the type of amine | This test serves as an additional confirmation of the presence of the active ingredient in Tamiflu ®, because oseltamivir contains a primary amine. |
| 4 | Iodine Indicator (10 uL) | Starch and Vitamin C | Starch brown to dark purple/black Vitamin C brown to colorless | Starch is present in genuine Tamiflu ® drugs, whereas Vitamin C is found as a filler in poor quality Tamiflu ® drugs. |
| 5 | Aluminon (10 uL) | Aluminum | light yellow to dark red | Poor quality Tamiflu ® drugs may have aluminum (aluminum oxide) present. |
| 6 | Folin-Ciocalteu (10 uL) | Acetaminophen and Vitamin C | Acetaminophen yellowish to greenish color Vitamin C yellow to dark blue | Both acetaminophen and Vitamin C have been found to be present in fake Tamiflu ® drugs, thus this test would indicate a poor quality Tamiflu ® drug. Acetaminophen may be substituted for the active ingredient oseltamivir phosphate and Vitamin C may be present as a substitute filler. |
| 7 | Biuret (10 uL) | beta-Lactams and Clavulanic acid | beta-Lactam blue to red/purple Clavulanic acid blue to green | Poor quality Tamiflu ® drugs may have beta-lactam antibiotics as substitutes for the active ingredient. Clavulanic acid is often used in combination with beta-Lactam antibiotics to overcome certain types of antibacterial resistance, so its presence would indicate a poor quality TAMIFLU ® drug. |
| 8 | Dithizone (10 uL) | Heavy metals | yellow-orange to purple (silver and cobalt), pink (zinc and lead), gray (nickel and copper), or purple (tin) | Poor quality drugs may have aluminum and/or heavy metals present, thus these indicators would indicate a poor quality Tamiflu ® drug. |
| 9 | Universal Indicator (10 uL) | Solvent pH Control | orange to red (low pH) or green (high pH) | This serves as a quality control spot for the diluent used. Both a low and high pH would indicate a problem with the solvent. |

Circle 1—Detecting Oseltamivir Phosphate

Oseltamivir phosphate is the active ingredient in Tamiflu®. This colorimetric test was adapted from that in the Michael Green et al. literature article (*Emerging Infectious Diseases*, Vol. 14, No. 4, April 2008). The most distinct color change was observed using a 3.45E-3M bromochlorophenol blue salt solution.

Circle 2—Detecting Phosphates and Chlorides

The silver(I) nitrate test is a common qualitative test for inorganic phosphates and chlorides. Silver(I) forms a yellow precipitate with phosphates and a white precipitate with chlorides. The most distinct color change was observed when 10 uL of 0.2M silver(I) nitrate solution was placed onto the paper and then dried in a 110° C. oven for 40 min.

Circle 3—Detecting Amines

Various amines undergo an oxidation with this oxidizing agent. The most distinct color change was observed when 10 uL equal parts of 0.1M iron(III) chloride and 0.1M potassium ferricyanide solution was used.

Circle 4—Detecting Starch and Vitamin C

An iodine test was developed to detect starch, which is often found in legitimate Tamiflu® pills. The triiodide ion locates itself inside of the amylose ring of the starch molecule and forms a dark purple/black colored complex indicating a positive result for starch (deep blue at the top of each lane). This test provides the PAD with an alternate method to verify the authenticity of a pill. Tamiflu® pills require the presence of cornstarch in their original recipe; therefore, a negative test indicates a low quality product.

Ascorbic acid/Vitamin C is found as a filler in low quality Tamiflu® products. In order to detect Vitamin C, it is necessary to adapt the known titration of ascorbic acid. Iodine is a powerful oxidant and Vitamin C is an anti-oxidant. As a result, the combination of the two produces a colorimetric change rapidly. The mixture of Vitamin C and starch/iodine mixture produces a quenching of any color to white. This occurs because the iodine molecule delocalizes itself from the amylose ring to react with Vitamin C, thus quenching the dark purple/black color typically seen with starch.

Circle 5—Detecting Acetaminophen or Vitamin C

Acetaminophen and Vitamin C are common substituent found in low quality Tamiflu® drugs. The Folin-Ciocalteu reagent contains a mixture of phosphomolybdate and phosphotungstate. Upon reaction with phenols, the substance changes from a light green to a dark green/blue color, which absorbs at 765 nm. The Folin-Ciocalteu indicator changes color in the presence of acetaminophen from a yellowish to greenish color. Vitamin C was found to produce a dark blue in the presence of Folin-Ciocalteu.

Circle 6—Detecting Aluminum

Aluminon is a dye commonly used in qualitative inorganic analysis to detect aluminum. It forms brilliantly colored lake pigments with aluminum (dark red lake), and also chromium, iron, and beryllium ions. In the TAMIFLU® PAD, aluminon is used to detect aluminum in dirt (e.g., aluminum oxide), which may be found in low quality Tamiflu® drugs. The most distinct color change was observed when 10 uL of aluminon solution was used.

Circle 7—Detecting Beta-Lactams (Antibiotics) or Clavulanic Acid

Poor quality Tamiflu® drugs may have beta-lactam antibiotics as substitutes for the active ingredient. Clavulanic acid, often used in combination with beta-lactam antibiotics to overcome certain types of antibacterial resistance, will also indicate a poor quality Tamiflu® drug. The most distinct color change was observed when 10 uL of the biuret reagent solution was used. This solution is made by combining 1.0058 g copper(II) sulfate pentahydrate with 3.0104 g sodium potassium tartrate, and then diluting to a total volume of 25 mL with 9M sodium hydroxide. A colored reaction is a result of the formation of a colored coordination complex of the copper(II) ion with the planar beta-lactam amide present in both the beta-lactam antibiotic (red/purple colored complex) and the clavulanic acid (green colored complex). The differences in the configuration of the complex are thought to yield the difference in color.

Circle 8—Detecting Heavy Metals

Dithizone is commonly used in qualitative inorganic analysis to detect heavy metals, including silver, zinc, cobalt, nickel, lead, tin, copper, mercury, and bismuth. These metals are clearly an indication of a low quality pharmaceutical. The most distinctive color change was observed when 10 uL of 0.1% dithizone (dissolved in carbon tetrachloride) followed by a drop of 25% ammonium hydroxide is placed on the paper.

Circle 9—pH Control 10 uL of universal indicator, common pH indicator, is used as a form of quality control of the diluent. If the water's pH is low or high, this raises concern about the quality of the pill test.

Example 3

Artemisinin Combination Therapies (ACT) PAD

Malaria is a life-threatening disease that plagues the developing world, especially the tropical regions of Africa and Asia. It is estimated that half the world's population is at risk for contracting malaria and that malaria is one of deadliest infectious diseases worldwide. This statistic is particularly devastating since malaria is a preventable and curable illness. One factor that contributes to the deadliness of this treatable illness is the prevalence of low quality drugs.

Artemisinin-derivative compounds such as artesunate (AS) and artemether (AM) are the most effective pharmaceuticals for treatment of malaria. They are best administered in combination with another antimalarial such as amodiaquine or lumefantrine. These treatments are known as artemisinin combination therapies (ACTs); they are the most potent and highly recommended treatment for *Plasmodium falciparum* malaria infection. Unlike chloroquine, the malaria parasite has not yet gained widespread resistance to ACTs, allowing them to remain effective. One of the reasons that two drugs are administered simultaneously is that AS and AM are powerful anti-malarials but have a short half-life in the body. Amodiaquine and lumefantrine have much longer half-lives and, in high concentrations, kill the remaining parasites that were not initially destroyed by AS or AM.

Low quality ACT pharmaceutical products may contain low amounts of AS/AM or none at all. Although drugs containing no AS/AM result in treatment failure, which can lead to death, the underdosed drugs are even more damaging because malarial parasites are exposed to but not killed by these underdosed drugs, which can lead to widespread resistance—the cause of the inefficacy of traditional anti-malarials such as quinine and chloroquine. Thus, the validation of antimalarial drugs is paramount in preserving the efficacy of this treatment. The legitimacy of anti-malarials can easily be tested in a laboratory by HPLC or mass spectrometry. However, the areas of the world most affected by malaria (and by low quality antimalarial drugs) are some of the poorest nations on earth. A family that spends what little money it has to buy these medications will not have the funds or the time to send these drugs to a far off laboratory in hopes of a positive result some weeks or months later. Even the pharmacy selling the drugs would be hard-pressed to find the resources for such a process. Additionally, anti-malarials are often sold in street markets rather than pharmacies, which are even less carefully regulated. Thus, the development of a low cost, low-tech test that could differentiate real drugs from low quality imitators could help save the lives of thousands.

The ACT PAD includes chemical indicators for the artemisinin drug (the primary drug of interest) as well as the partner drugs amodiaquine, lumefantrine, chloroquine, and sulfadoxine. Presence of only a partner drug is highly indicative of a counterfeit composition, as there is either widespread resistance to the drug, or the drug is not effective enough on its own to cure a malarial infection. The ACT PAD also tests for the excipient starch and the common counterfeit ingredients acetaminophen, amoxicillin, ampicillin, and sulfates. These are often included in low quality pharmaceutical products to deceive the consumer. Also, even if a pharmaceutical product tests positive for artesunate or artemether, the presence of acetaminophen and/or an antibiotic will alert the user of the potential low quality of the drug.

The following is a description of one embodiment of an ACT PAD.

Lane A—Detecting Artesunate, Artemether, Dihydroartemisinin, and Erythromycin

Reagent: 25 mg/mL fast blue RR salt (FBS) in 3 M $H_2SO_4$ (4 uL)

Other chemical indicators for artemisinin derivatives may include ferrous thiocyanate or 2,4-dinitrophenylhydrazine, but FBS is the most preferred indicator. FBS turns from yellow to blue/gray in the presence of the artemisinin derivatives artesunate, artemether, and dihydroartemisinin. It does not change color in the presence of the parent compound artemisinin; this is desirable as artemisinin is not a valid treatment for malaria, but the derivates are. The blue/gray color change therefore indicates a good antimalarial pill composition. FBS turns robin's egg blue in the presence of erythromycin; by including positive controls on future ACT PAD embodiments, confusion between erythromycin and artemisinin derivatives can be avoided. The FBS reaction was gleaned from prior literature (Ioset, Jean-Robert, Harparkash Kaur. "Simple field assays to check quality of current artemisinin-based antimalarial combination formulations." *PLoS ONE* 4: e7270). International application No: PCT/GB2007/000012 discloses use of FBS as a field test for determining artemisinin derivatives, but does not include a library of chemical tests for determining overall drug quality as disclosed herein.

It has been found that when FBS is dissolved in sulfuric acid, it yields the best color change, as compared with the results obtained when FBS is dissolved in other solvents such as methanol and water. Unlike many other PAD reactions, the FBS reaction takes roughly one hour to develop. FBS, a diazonium salt, is photolabile; for this reason, ACT PADs must be stored in a dark environment until the time of use. The 3 M $H_2SO_4$ in which the FBS is dissolved causes the paper of the PAD to degrade quite quickly. For this reason, an ACT PAD should be used within one week of having been treated with FBS reagent. In the future, this lane test will be adapted to create a semi-quantitative spot test, thus addressing the issue of underdosed artemisinin derivative drugs.

Lane B—Detecting Amodiaquine and Chloroquine

Reagent: 2 M cobalt thiocyanate in $H_2O$ (4 uL).

Amodiaquine is often used as a partner drug with artesunate in ACT drug formations. Cobalt thiocyanate produces a distinct blue to green color change in the presence of amodiaquine, which makes it a prime candidate for amodiaquine detection in the field. Additionally, cobalt thiocyanate is relatively nontoxic and stable in ambient conditions, unlike many other indicators such as diazonium salts. Utilizing the FBS indicator on a paper analytical device provides a low-tech colorimetric test that could be used in developing countries by non-scientists to determine the legitimacy of antimalarial combination therapies. As the cobalt thiocyanate indicator also produces the same blue to green color change in the presence of several other compounds (e.g., cocaine), additional tests are included in the PAD to safeguard the accuracy of these paper analytical devices.

Chloroquine is an old drug that is no longer recommended for treatment of severe malaria, as the *P. falciparum* malaria bacteria has developed a widespread resistance to it. It can also be tested for using the cobalt thiocyanate reagent. Cobalt thiocyanate turns from pink to bright aqua blue in the presence of chloroquine. This is noticeably different from the green produced by the cobalt thiocyanate+amodiaquine reaction, so the two drugs (amodiaquine and chloroquine) are easily distinguishable from one another.

Lane C—Detecting Sulfadoxine

Reagents: 0.35 M 2-napthol (4 uL), 1M sodium hydroxide (4 uL), 0.5 M tosic acid (4 uL), 0.4 M sodium nitrite (4 uL)

Sulfadoxine is an antimalarial drug that is no longer used on its own, but is sometimes present in ACT formulations. With the given set of reagents, lane C turns from yellow to red in the presence of sulfadoxine. The chemistry is as follows: within the lane, tosic acid and sodium nitrite combine to form nitrous acid. This diazotizes the sulfadoxine, forming an $N^{2+}$ leaving group. Sodium hydroxide deprotonizes the 2-napthol, which then does nucleophilic aromatic substitution with the $N^{2+}$ group to form a red compound. The sensitivity of this test is 95.8% (23 of 24 samples) and the specificity is 98.0% (151 of 154 samples).

Lane D—Detecting Lumefantrine and Vitamin C

Reagents: 2% starch indicator solution (4 uL), $I_3$ (4 uL)

Lumefantrine is a common partner drug with artemether in ACT formulations. Vitamin C is a commonly found fake drug excipient. In the presence of both lumefantrine and vitamin C, the color of blue $I_3$ will be quenched so that no color shows in lane D. The chemistry here is similar to that described in lane 3 of the acetaminophen PAD.

Lane E—Detecting Acetaminophen

Reagent: 2 M ferric chloride in $H_2O$ (4 uL)

This reaction is that same as that described in lane 2 of the acetaminophen PAD. It is important to test for acetaminophen on an ACT PAD because analgesics are commonly included in counterfeit pill formulations in order to reduce pain/fever and deceive the consumer.

Lane F—Detecting Acetaminophen and Amoxicillin

Reagents: 0.1M sodium hydroxide (4 uL), 30 mg/mL sodium nitrite (4 uL), 10 mg/mL nitroaniline in 1M tosic acid (4 uL)

This set of reagents turns from colorless to orange in the presence of amoxicillin and/or acetaminophen. Neither amoxicillin, an antibiotic, nor acetaminophen should be present in an authentic ACT drug formulation.

Lane G—Detecting Starch

Reagent: $I^{3-}$ and povidone (4 uL)

This reagent turns light brown to black in the presence of starch, with chemistry similar to that in lane 3 of the acetaminophen PAD. Starch is a commonly found authentic drug excipient.

Lane H—Detecting Ampicillin and Amoxicillin

Reagent: 5 mM TCNQ in acetonitrile (4 uL)

This reagent turns from yellow to blue/green in the presence of ampicillin and/or amoxicillin. Neither of these antibiotic drugs should be present in an ACT drug formulation.

Lane I—Detecting Ampicillin and Amoxicillin

Reagents: saturated ninhydrin in acetonitrile (4 uL), 1 g/5 mL potassium carbonate This set of reagents turn from colorless to orange in the presence of ampicillin and from colorless to green or purple in the presence of amoxicillin. This is provided as another method of detection in addition to that given in lane H. This colorimetric reaction takes roughly 10 minutes to develop.

Lane J—Detecting Sulfates

Reagents: 0.1M barium chloride (4 uL), 25 mM Rhodizonate (4 uL)

These reagents turn from pink to colorless or yellow in the presence of sulfates. Sulfates are a commonly found counterfeit ingredient, as they are present in wallboard (gypsum), which may be ground up and pressed into a pill.

Lane K—Sulfate Test Control

Reagents: 0.1M barium chloride (4 uL), 0.1 M ferric ammonium sulfate (4 uL), 25 mM Rhodizonate (4 uL)

This lane is pre-treated with sulfates, so it should always turn from pink to colorless or yellow. This exists to ensure that the chemicals are acting properly, as the chemistry of this test is known to be unstable.

Lane L—Timer Lane

Reagents: nickel(II) (4 uL), diglyoxime (4 uL), 2% starch indicator (4 uL), $I_3$ (4 uL)

These reagents turn from colorless to red when water reaches the top of the PAD, regardless of what chemical components are in the drug formulation. When the red color is observed, this indicates to the user that the PAD can be removed from the water.

Figure 10:
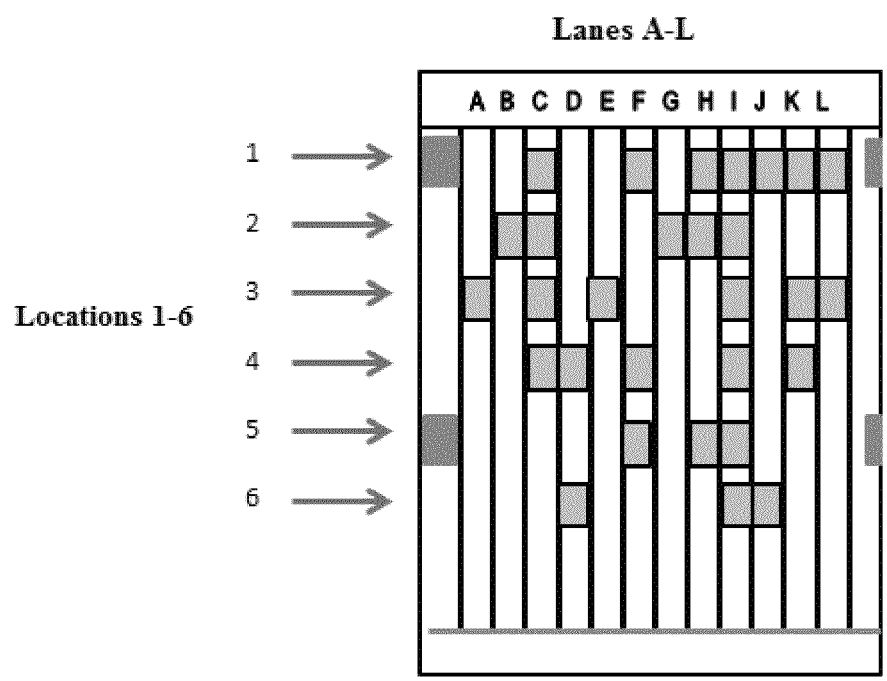
FIG. 10 depicts a Artemisinin Combination Therapies (ACT) PAD according to one embodiment.

One embodiment of the ACT PAD is shown in FIG. 10. Each lane (A-L) tests for a specific chemical. Locations 1-6 exist to indicate where reagents must be applied within the lanes. A grey box indicates that a chemical reagent is applied to that location. The pill of interest is swiped across all lanes (A-L), beginning at the orange boxes at locations 1 and 5.

The order in which chemicals are spotted can be seen in Table 3. Table 3 corresponds directly with FIG. 10. The number to the left of the reagent indicates the location of the reagent, and "swipe" is written where a pill swipe is present (always in lanes 1 and 5). The + and − signs indicate what a positive and negative reaction for that lane look like.

TABLE 3 location of reagents on ACT PAD

| Lane A | AM/AS/DHA Test | | Lane B | Co(SCN)2 | | Lane C | Sulfadoxine Test |
|---|---|---|---|---|---|---|---|
| Loc. | 1 | Pill Swipe | Loc. | 1 | Pill Swipe | Loc. | 1 | 2-naphthol (0.35M), 4 µL (swipe) |
| | 2 | | | 2 | Co(SCN)2 (2M), 4 µL | | 2 | NaOH (1M), 4 µL |
| | 3 | 25 mg/mL FBS in 3M $H_2SO_4$, 4 µL | | 3 | | | 3 | HOTs (0.5M), 4 µL |
| | 4 | | | 4 | | | 4 | $NaNO_2$ (0.4M), 4 µL |
| | 5 | (swipe) | | 5 | (swipe) | | 5 | Pill Swipe |
| | 6 | | | 6 | | | 6 | |
| | + | (AM/AS/DHA) Dark grayish blue | | + | Chloroquine = aqua, Amodiaquine = green | | + | Red with sulfadoxine |
| | + | (Erythromycin) Robin's egg blue | | − | orange/pink | | − | Yellow |
| | − | yellow (from reagent) | | | | | | |

| Lane D | Lumefantrine Test | | Lane E | FeCl3-No Soap | | Lane F | Nitroaniline |
|---|---|---|---|---|---|---|---|
| Loc. | 1 | (swipe) | Loc. | 1 | swipe | Loc. | 1 | 4 uL 0.1M NaOH & Swipe |
| | 2 | | | 2 | | | 2 | |
| | 3 | | | 3 | 2M FeCl3 solution, 4 uL | | 3 | |
| | 4 | 2% Starch indicator soln, 4 µL | | 4 | | | 4 | NaNO2 (30 mg/mL), 4 uL |
| | 5 | Pill Swipe | | 5 | swipe | | 5 | 10 mg/mL nitroaniline in 1M HOTs, 4 uL |
| | 6 | 13, 4 µL | | 6 | | | 6 | |
| | + | No color | | + | grey running up lane = acetaminophen | | + | Acetaminophen, amoxy = orange |
| | − | Blue | | − | slight yellow coloration from spot = negative | | − | no color |

| Lane G | Starch Test | | Lane H | TCNQ | | Lane I | Ninhydrin Test |
|---|---|---|---|---|---|---|---|
| Loc. | 1 | Pill Swipe | Loc. | 1 | 4 uL, 5 mM TCNQ in acetonitrile w/ Swipe | Loc. | 1 | Swipe + 4 µL Ninhydrin sat in CH3CN |
| | 2 | I3-/Povidone, 4 uL | | 2 | 4 uL, 5 mM TCNQ in acetonitrile | | 2 | 4 µL Ninhydrin sat in CH3CN |
| | 3 | | | 3 | | | 3 | 4 µL Ninhydrin sat in CH3CN |
| | 4 | | | 4 | | | 4 | 4 µL Ninhydrin sat in CH3CN |
| | 5 | Pill Swipe | | 5 | 4 uL, 5 mM TCNQ in acetonitrile w/ Swipe | | 5 | Swipe + 4 µL Ninhydrin sat in CH3CN |
| | 6 | | | 6 | | | 6 | 4 µL 1 g/5 mL K2CO3 take >10 minutes to form color for imaging/best at top of lane |
| | + | purple/black = starch | | + | blue/green = amp, amoxy, | | + | Amp = orange, Amoxy = green or purple? |
| | − | tan/brown | | − | yellow | | − | no color |

| Lane J | Sulfate Test | | Lane K | Sulfate Test control | | Lane L | Timer |
|---|---|---|---|---|---|---|---|
| Loc. | 1 | .1M BaCl2, 4 uL | Loc. | 1 | .1M BaCl2, 4 uL | Loc. | 1 | Ni2+, 4 uL |

TABLE 3-continued

| | | | | | |
|---|---|---|---|---|---|
| 2 | | 2 | | 2 | |
| 3 | | 3 | 0.1M Fe(II)(NH4)2SO4, 4 uL | 3 | diglyoxime, 4 uL |
| 4 | | 4 | 25 mM Rhodizonate 4 uL | 4 | |
| 5 | Pill Swipe | 5 | swipe | 5 | |
| 6 | 25 mM Rhodizonate 4 uL | 6 | | 6 | 2% starch indicator |
| | | | | I3 | |
| + | Colorless or yellow | + | Colorless or yellow | + | Stop run when red appears |
| − | Pink | − | Pink | − | |

Example 4

Devices for Analysis of Tuberculosis (TB) Medications, Including Combination Medications Tuberculosis (TB) is a disease that is usually treated with combinations of the "first line" medications isoniazid, rifampicin, pyrazinamide, and ethambutol. Combinations are used because many strains of TB are resistant to one or more of the first-line drugs, so for determining drug quality, it is important to determine whether each of the expected active pharmaceuticals is present. The TB PAD aims to determine if the correct components of a TB drug are present, and further to determine if any unauthorized or substitute pharmaceuticals or excipients are present.

The following are the chemical structures for the four active pharmaceuticals commonly used to treat TB:

Rifampicin

Pyrazinamide

Ethambutol

Isoniazid

Figure 4:
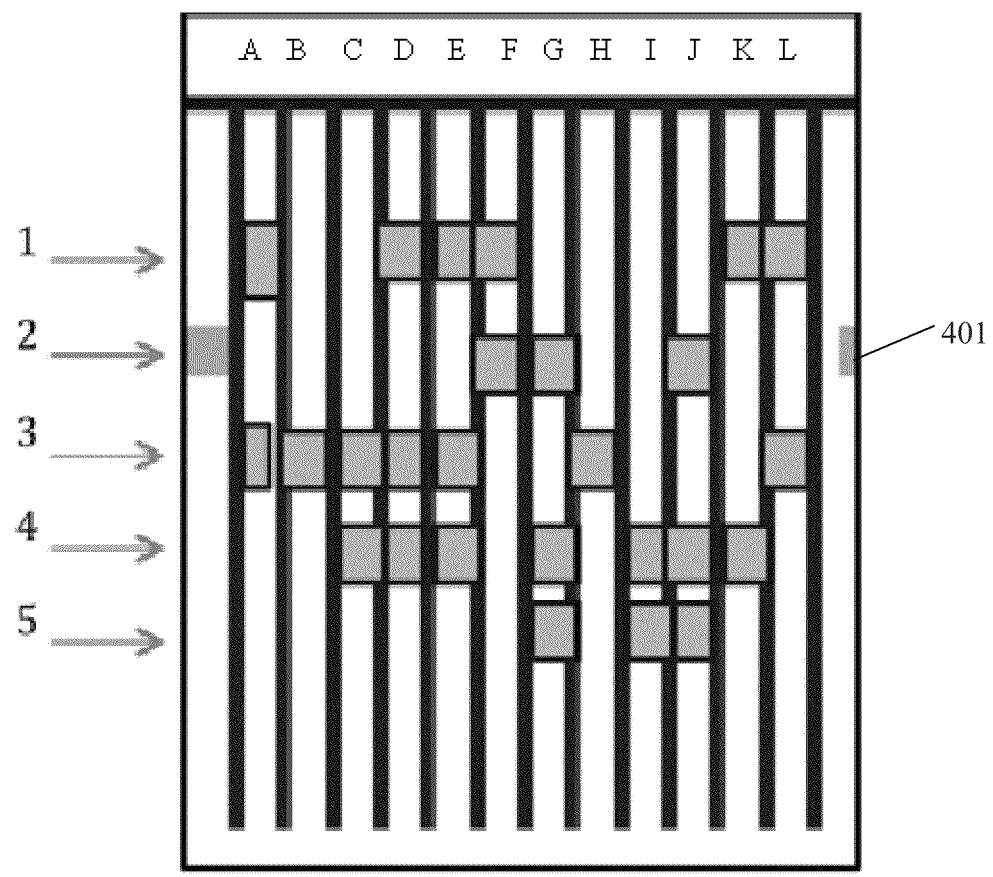
FIG. 4 depicts a tuberculosis (TB) PAD according to one embodiment.

As shown in FIG. 4, this PAD for the detection of components of TB treatments and excipients is prepared by placing 2-8 μL (preferably 4 ul) of each of the following reagents in the designated locations on a paper analytical device that has 12 lanes defined by hydrophobic separators that completely penetrate the thickness of the underlying porous substrate Ahlstrom 319, and the separators are formed by the wax printing method. The placement of the reagents can be done in many ways, including deposition of individual portions of reagent via capillary pipettes, automatic pipets (e.g., Eppendorf Pipetman), rods or arrays of rods to deliver droplets of reagent to specific locations (a "frog" device), and serial or parallel solution handling robots such a Biomek 96-well plate replicating robot.

TABLE 4

Lanes and reagents of the TB PAD.

| Lane | Row | Reagent | Concentration |
|---|---|---|---|
| A | 1 | Potassium carbonate | Saturated |
| A | 3 | Copper sulfate | 1M |
| B | 3 | Iron (III) nitrate | 1M |
| C | 3 | Sodium nitroprusside | 10% w/v |
| C | 4 | Sodium hydroxide | 1M |
| D | 1 | 2,2'-bypyridine | 1M |
| D | 3 | Manganese dioxide | Saturated* |
| D | 4 | Ammonium iron (III) sulfate dodecahydrate | 1M |
| E | 1 | 2,2'-bypyridine | 1M |
| E | 2 | Isoniazid | Saturated |
| E | 3 | Manganese dioxide | Saturated* |
| E | 4 | Ammonium iron (III) sulfate dodecahydrate | 1M |
| F | 1 | Tetracyanoquinodimethane in acetonitrile | 5 mM |
| F | 2 | Tetracyanoquinodimethane in acetonitrile | 5 mM |
| G | 2 | Sodium hydroxide | .1M |
| G | 4 | Sodium nitrite | 30 mg/mL |
| G | 5 | nitroaniline in 1M HOTs | 10 mg/mL |
| H | 3 | Triiodide and Povodone | Saturated |
| I | 4 | 2 parts Iron (III) chloride, 1 part soap | 2M |
| I | 5 | 2 parts Iron (III) chloride, 1 part soap | 2M |
| J | 5 | Iron (III) chloride | 2M |
| K | 1 | Rhodizonate | .1M |
| K | 4 | Barium chloride | .1M |
| L | 1 | Nickel chloride | .2M |
| L | 3 | diglyoxime | .4M |

As shown in FIG. 4, each lane is labeled with a letter. Each reagent is placed in a designated place indicated by the numbers and arrows in each lane. Each spotting location is 9 mm from its neighbors in the lane. For example, the two reagent spots in lane C are 9 mm apart. This distance is due to the settings on the solution handling robot; the drops could be placed anywhere from 2 mm to several cm apart for other applications or deposition systems. The tests in Lanes have consistently been able to detect as little as 0.01 g of the substance applied to the PAD. In some tests, the resulting color was lighter, but it was still the correct color. All lanes of the PAD except the nitroaniline test in Lane G and the sulfate test in Lane K lasted at least 2 weeks at room temperature in a plastic zipper-top bag.

Lane A—a Test for Ethambutol Using Cu(II) and $CO_3^{2-}$.

Royal Blue appearing as a chromatographically mobile band (at or near the top of the lane) indicates ethambutol. When ethambutol is combined with other TB drugs, different colors are also observed. For example, isoniazid produces a minty green color at the swipe line (401) (not chromatographically mobile) and rifampicin gives the bright orange color of rifampicin at the swipe line (401) plus a purple color with moderate chromatographic mobility that usually covers only half of the space between the swipe line and the top of the lane. Pyrazinamide does not interfere with the test. Other colors indicate the presence of other pharmaceuticals or excipients, to with:

(i) Beta lactam antibiotics, such as amoxicillin and ampicillin, give a dark forest green color at the top of the lane, (ii) Salicylic acid gives a bright lime green color with low chromatographic mobility (mostly at the swipe line), (iii) rifampicin gives the bright orange color of rifampicin at the swipe line plus a purple color with moderate chromatographic mobility that usually covers only half of the space between the swipe line and the top of the lane, and (iv) isoniazid gives a leaf green color at the swipe line.

A negative test result is obtained with excipients including: acetaminophen, starch, talc, lactose, aspirin, baking soda, chalk, and gypsum and appears as a pale to dark turquoise color covering usually half to the entire distance from the Cu to the top of the lane. This color is due to aqueous Cu(II) and/or Cu(II) carbonate complexes.

This test works best when it has been allowed to run all the way to the top of the lane.

Sensitivity for ethambutol: 24/24 tests containing ethambutol correctly indicated the presence of ethambutol in lab validation trials, 100%

Selectivity for ethambutol: 101/103 tests that did not contain ethambutol did not indicate the presence of ethambutol, 98%.

Lane B—a Test for Rifampicin Using Fe(III) Nitrate.

Rifampicin alone or in combination with 1-3 other TB drugs gives a dark orange or smokey red color at the swipe line (401) plus a dark brown or black color in the area between the swipe line and the top of the lane.

Ampicillin and amoxycillin give a pale grey color in the area between the swipe line and the top of the lane. Lane A is a more reliable test for the presence of beta lactam antibiotics but this can provide backup information.

Salicylic acid (present in degraded aspirin) gives a black color in the area between the swipe line (401) and the top of the lane with dark purple at the swipe line (401).

A negative test (obtained with acetaminophen, starch, talc, lactose, aspirin, baking soda, chalk, and gypsum) will appear as yellow or pale orange colors along the lane.

This test is a reliable measure for the presence or absence of rifampicin.

Sensitivity for rifampicin: 30/30 tests containing correctly indicated the presence of rifampicin, 100%

Selectivity for rifampicin: 86/98 tests that did not contain rifampicin did not indicate the presence of ethambutol, 88%

All of the false positives could be distinguished from genuine positives by consideration of other lane results (e.g., salicylic acid can be ruled out because of its positive nitroaniline test).

Lane C—a Test for Pyrazinamide Using Sodium Nitroprusside and NaOH

Pyrazinamide (either alone or combination with ethambutol, rifampicin, or isoniazid) gives a coral red or peach color in the area between the swipe line (401) and the top of the lane.

Isoniazid, either alone or in combination with ethambutol or rifampicin, gives a dark orange color in the area between the swipe line and the top of the lane.

Rifampicin alone gives a dark purple red color.

A negative test is obtained with common excipients and substitute pharmaceuticals such as acetaminophen, starch, talc, lactose, aspirin, baking soda, chalk, and gypsum, and appears as lemon yellow to pale yellow color in the lane.

Sensitivity for pyrazinamide: 24/26 tests containing Pyrazinamide correctly indicated the presence of pyrazinamide, 92%

Selectivity for pyrazinamide: 99/102 tests that did not contain pyrazinamide did not falsely indicate the presence of pyrazinamide, 97%

Sensitivity for isoniazid: 13/20 tests containing isoniazid correctly indicated the presence of isoniazid, 92%

Selectivity for isoniazid: 108/108 tests that did not contain isoniazid did not falsely indicate the presence of isoniazid, 100%

Sensitivity for rifampicin: 24/29 tests containing rifampicin correctly indicated the presence of rifampicin, 83%

Selectivity for rifampicin: 86/98 tests that did not contain rifampicin did not indicate the presence of rifampicin, 88%

Lane D—a Test for Isoniazid Using Fe(III), $MnO_2$, and Bipyridine

Isoniazid either alone or in combination with ethambutol or pyrazinamide gives a red color at the top of the lane. Other drugs or excipients tested gave either no color or pale yellow color from Fe(III). Rifampicin interfered with this test due to its strong orange color. This test may be replaced by a test involving napthoquinone sulfonate.

Isoniazid contains an acyl hydrazine group which can reduce Fe(III) to Fe(II). Fe(II), but not Fe(III), forms a dark red complex ion with 3 molecules of bipyridine. Although one skilled in the art might expect Fe(III) to be stable on the PAD surface, in fact a high level of false positive was observed after 1-3 days of storage of the PAD, indicating that perhaps the cellulose in the paper contains enough reducing groups that some of the Fe(III) is reduced during storage on the PAD. In order to prevent this false positive result, a suspension of the oxidant manganese dioxide was placed on the lane in a location such that the Fe ions traversed the oxidant zone before encountering the drug swipe.

Sensitivity for isoniazid: 22/30 tests containing isoniazid run in lab which correctly indicated the presence of isoniazid, 73%

Selectivity for isoniazid: 80/97 tests that did not contain isoniazid did not indicate the presence of isoniazid, 82%

Lane E—a Control Lane for Isoniazid with Isoniazid, $FeNH_4$, $MnO_2$ and Bipy.

Isoniazid turns the top of the lane or the whole lane red.

This test is a control lane that turns red in every situation. It should provide a comparison for the Lane D, to determine if Isoniazid is present.

Reliability of control lane: 127/127 tests functioned correctly. The reliability of this lane indicates that all of the reagent spots were correctly applied by the spotting robot; and the error rate is less than 0.3%.

Lane F—a Test for Acetaminophen Using TCNO.

Acetaminophen is a substitute pharmaceutical which may be present in fake TB formulations. It contains an electron-rich phenol that can partially reduce TCNQ, forming a blue/green compound. This test was either light yellow or clear in every situation, including with acetaminophen.

Lane G—a Test for Acetaminophen and Amoxicillin Using Nitroaniline Tosic acid $NaNO_2$, and NaOH Acetaminophen gives a dark orange or peach color while isoniazid and isoniazid in combination with ethambutol give yellow colors. The sodium nitrite is acid-sensitive and stable for only 2-3 days on the PAD when it is stored in air.

Sensitivity for acetaminophen: 6/7 tests containing acetaminophen correctly indicated the presence of acetaminophen, 86%

Selectivity for acetaminophen: 101/101 tests that did not contain acetaminophen did not indicate the presence of acetaminophen, 100%

It is difficult to differentiate between peach (expected outcome) and gold, yellow, beige, and other close shades of these.

Lane H—a Test for Starch Using $I_3$/Povodone

The starch sample gives a black or dark blue/brown color at the swipe location, which may look spotty or appear only on the surface of the powder.

Lane I—a Test for Rifampicin and Salicylic Acid Using $FeCl_3$ and ⅓ Soap

Salicylic acid, rifampicin, rifater, rifampicin and isoniazid turns the bottom of this lane smokey red on black while rifampicin and Pyrazinamide, as well as ethambutol and rifampicin, produce color at the top of the lane.

Acetaminophen gives a gray or black color without any red streaks.

This test is very similar to lane B.

Lane J—a Test for Carbonate and Salicylate

Acetaminophen gives a gray color while Rifampicin, ethambutol and rifampicin, rifampicin and isoniazid, and rifampicin and Pyrazinamide give a dark black color at the swipe line. Carbonate gives a dark orange color at the swipe line, and salicylate (found in degraded aspirin) gives a mobile purple color.

This lane contains $FeCl_3$.

Lane K—a Test for Sulfate Using $BaCl_2$ and Rhodizonate.

Ethambutol gives black or gray at the bottom of the lane while rifampicin (or a combo containing rifampicin) gives yellow or gold.

Lane L—a Timer with Diglyoxime.

This lane turns pink with everything except compounds containing rifampicin, and turns coral with rifampicin. This test worked consistently. It is a timer that turns a strong pink color to tell the person using the test when to remove the bottom of the paper from the water. 137/137 of the timers worked correctly.

It should be noted that Lanes B, I and J have similar outcomes because they all have iron in them. Most importantly, acetaminophen will give a false positive for rifampicin in Lane B, but rifampicin is easy to identify because of its red color which spreads to be yellow in most lanes.

TABLE 5

Color Combo Tables listing what colors are seen in each lane when the TB PAD was run using 23 different substances (11 combinations of TB drugs, 12 excipients or substitute pharmaceuticals).

| | | | Lanes A-E | | |
|---|---|---|---|---|---|
| Pure Drug: | Ethambutol Lane (A): | Rifampicin Lane (B): | Pyrazinamide Lane (C) | Isoniazid Lane (D) | Isoniazid Control Lane (E) |
| Acetaminophen | Light Turquoise | Black | yellow | Clear | Red-top |
| Amoxicillin | turquoise if a little is applied, navy at drug and dark green-top if a lot is applied | Brown-top | Yellow | Clear, one has faint pink-top | Red-top |
| Ampicillin | Turquoise | Gold top | Yellow | Clear, two have faint pink-top | Red-top |
| Aspirin | turquoise | Gold | yellow | Clear | Red-top |
| Baking Soda | Light Turquoise | Gold | clear, some gray-yellow at top | Clear, sometimes there is light red at top | Red-top |
| Chalk | Light Turquoise | Gold | yellow | Clear | Red-top |
| Erythromycin | Turquoise (sometimes has light blue at top, one time gave a darker blue at top->FP) | Gold-top | Yellow, some black at top | Faint pink top/clear | |
| Ethambutol | Royal Blue-top | Gold-brown-top | faint yellow/orange | Clear, one has faint pink-top | Red-top |
| Ethambutol & Isoniazid | Royal Blue-top, if a lot of drug, then Green at drug | Peach | yellow-orange | Small amt of red at top | Red-top |

TABLE 5-continued

Color Combo Tables listing what colors are seen in each lane when the TB PAD was run using 23 different substances (11 combinations of TB drugs, 12 excipients or substitute pharmaceuticals).

| | | | | | |
|---|---|---|---|---|---|
| Ethambutol & Rifampicin | Turquoise-bottom, royal blue-top | Black, very top is green/orange/yellow | Burnt Orange/tan, some are maroon at bottom | Orange | |
| Gypsum | turquoise | Gold-top | Yellow | Clear | Gold, red-top |
| Isoniazid | Forest Green at bottom | Beige or gold | yellow-orange | Light red, Red | Red |
| Lactose | | Gold-top | Yellow | Clear | |
| Pyrazinamide | turquoise | Gold-top | Red | Clear | Red-top |
| Pyrazinamide & Ethambutol | Turquoise-bottom, royal blue-top | none | Red, if only a small amt is applied, it can look brown or burnt orange | Clear | |
| Pyrazinamide & Isoniazid | Turquoise | Beige, clear | red | Pink-Red | |
| Rifampicin | Navy-bottom, turquoise-top | brown/black | Brown | Orange, red/pink-top | |
| Rifampicin & Isoniazid | Royal or navy blue at BOTTOM, turquoise-top | Dark forest green | dark orange, top is gold, forest green, gray-gold, or burnt orange | YellowOrange-bottom, pink-top | |
| Rifampicin & Pyrazinamide | Navy-bottom, turquoise-top | Charcoal Gray/black | (Darker) Red | orange, pink top | |
| Rifater (Rif, Iso, Pyra) | Navy-bottom, turquoise-top | Dark forest green or olive green (definitely at top) | Dark red | Orange, pink at very top | |
| Salicylic Acid | Green-bottom | Smokey red bottom, red-top | Yellow | Clear, one has faint pink-top | Red-top |
| Talc | turquoise | Gold | Yellow, some black at top | Clear | Red-top |

| | Lanes F-L | | | | | |
|---|---|---|---|---|---|---|
| Pure Drug: | TCNQ (F) | Nitroanaline (G) | Starch Test (H) | FeCl3 ⅓ Soap (I) | FeCl3 Control (J) | Sulfate Test (K) | Time (L) |
| Acetaminophen | Clear or light yellow | Clear, light yellow | Gold-top | Clear | Gray/black | light gray | pink |
| Amoxicillin | Clear or light yellow | Light yellow or cream | Gold, light beige, or clear | Cream, beige, or clear | Brown, beige | Clear | pink |
| Ampicillin | Clear or light yellow | Clear, heavy-beige | Clear | clear | Gold-top | clear | pink |
| Aspirin | Light yellow | Light yellow | Gold-top | clear | Light yellow | clear | pink |
| Baking Soda | Clear, light yellow, orange, or brown | Light yellow or brown | Clear or gold | peach or clear | Gold | clear | pink |
| Chalk | Light yellow | light yellow | Gold | clear | Light yellow/beige top | clear | pink |
| Erythromycin | Clear | Clear, beige | Gold-top | clear | Light yellow, clear, or beige | clear | pink |
| Ethambutol | Light yellow | Clear | Gold or beige | clear or light beige | Beige | clear | pink |
| Ethambutol & Isoniazid | Clear | Yellow | Clear | clear or cream main | Gold, light yellow, beige, or clear | clear | pink |
| Ethambutol & Rifampicin | Gold | Clear | Gold, light yellow, beige, or clear | Black/Gray bottom | Black-main or bottom | Light yellow | Coral |

TABLE 5-continued

Color Combo Tables listing what colors are seen in each lane when the TB PAD was run using 23 different substances (11 combinations of TB drugs, 12 excipients or substitute pharmaceuticals).

| | | | | | | | |
|---|---|---|---|---|---|---|---|
| Gypsum | Clear | clear | Gold-top, beige | clear | Clear/beige | clear | pink |
| Isoniazid | Clear | Light yellow, yellow, or clear | Clear | peach, beige, maybe red-top | Beige | clear | pink |
| Lactose | Clear | clear | Gold or beige | Light beige/brown | Beige or brown top | clear | pink |
| Pyrazinamide | Clear | Clear or light beige | Gold-top | clear | olive green-top, light beige-top, or light gold-top | clear | pink |
| Pyrazinamide & Ethambutol | Clear | Clear | Gold, beige, or clear | clear, light beige/ gray-top | olive green-top, light beige-top, or light gold-top | clear | pink |
| Pyrazinamide & Isoniazid | Clear | Light-clear, heavy-yellow | Light yellow, clear | clear | Beige top | clear | pink |
| Rifampicin | Clear, light yellow, or orange | Yellow, clear, or beige gray | Yellow-top, or clear | Gray/Black/ Smokey Red | Black close to top, smoky red near bottom of some | yellow | red bottom, gold top |
| Rifampicin & Isoniazid | Gold | Light-gray yellow top, heavy-brown top | Gold, clear | Black-top | Gray/black bottom | yellow/gold | red bottom, gold top |
| Rifampicin & Pyrazinamide | Orange | Yellow-top | Gold-top | Black-top | Black top | yellow/gold | red bottom, gold top |
| Rifater (Rif, Iso, Pyra) | Yellow-orange | Brown top | Heavy-gold, light-clear or beige | Gray/black | Black | yellow/gold | red bottom, gold top |
| Salicylic Acid | Beige at bottom/clear | Light yellow or beige | Gold, beige, or clear | | Smokey red, black top | clear | pink |
| Talc | Light yellow | Beige/clear | Gold, beige, or clear | | Beige | clear | pink |

Example 5

Paper Analytical Device for Analyzing Beta Lactam Antibiotics

The β-Lactam PAD is designed to detect two of the active ingredients in antibiotics, namely, Ampicillin and Amoxicillin.

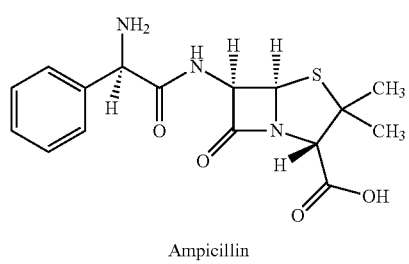

Ampicillin

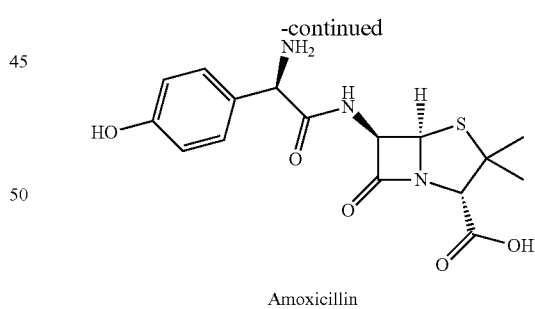

Amoxicillin

Figure 5:
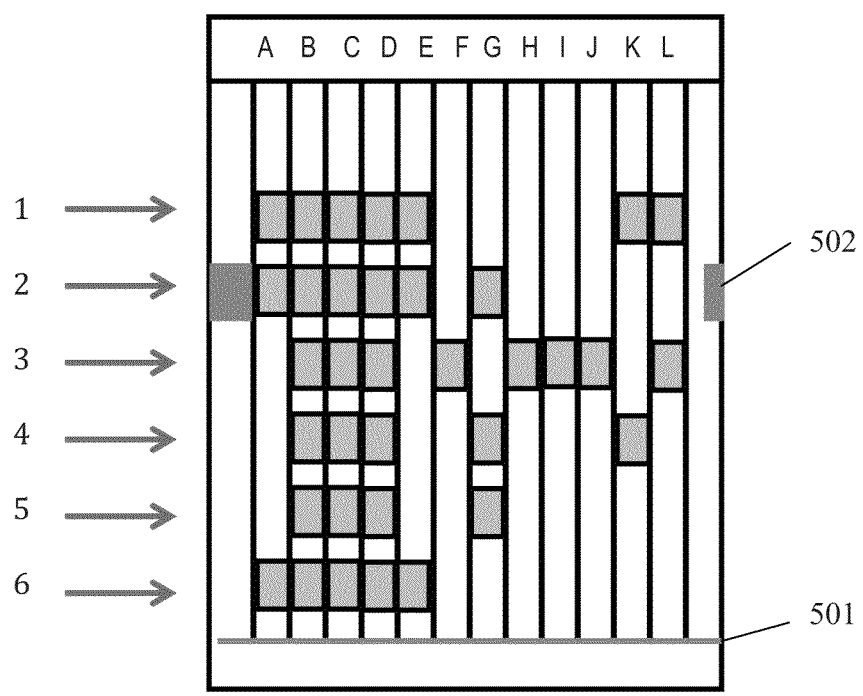
FIG. 5 is a diagram depicting a beta-Lactam PAD according to one embodiment.

As shown in FIG. 5, the β-Lactam PAD is made up of twelve different colorimetric chemical tests that are structured to analyze the contents of the antibiotic pills. The reagent placement on the PAD is summarized in Tables 6 and 7. Each reagent area in each lane is identified by its row number in Tables 6 and 7 corresponding to a location along the length of the lane, as shown by the numbered arrows pointing at grey rectangles in FIG. 5. In order to run the test, a tablet is scraped along the "swipe line" (indicated by arrow 2) on the PAD, at the level of the printed indicator marked 502, most effectively using a piece of metal or plastic screening or sandpaper to help remove powder from the tablet. The bottom edge of the PAD is then set in a shallow dish of water (usually deionized water, but several types of tap water were tested and also proved effective) up to the top of solvent zone 501. Water runs up the twelve lanes (A through L) by capillary action which initiates the chemical tests and produces colors characteristic of specific functional groups present in the targeted analytes. For example the lane containing ninhydrin to test for amoxicillin and ampicillin (lanes B, C and D) will turn orange if ampicillin is present and green if amoxicillin is present. If neither of these two are present, the lane will appear yellow. These colors may appear at different locations on the lanes after the pill in question has been scratched on the PAD and the water has run up all of the lanes via paper chromatography, forming a "color bar code" of the reactions, as shown in Table 8.

In Tables 6-7, the locations of the reagents are 9 mm from each other to accommodate our solution handling robot, thus Location 6 is at the bottom edge of the PAD (above the level of the water dip line of the solvent zone) and Location 5 is 9 mm above it in the same lane. Other locations are also possible; the spots can be placed as close as 2 mm or as far as several cm.

TABLE 8

Colors of positive results

| Lane | Analyte | Positive Result Color |
|---|---|---|
| A | ampicillin and amoxicillin | Green |
| B | ampicillin | Orange |
|   | amoxicillin | Green |
| C | ampicillin control | Orange |
| D | amoxicillin control | Green |
| E | reducing agents | Green to Blue |

TABLE 6

Placement of reagents on the β-lactam PAD, lanes A-F. The quantity of each reagent is 4 μL.

| Lane | A | B | C | D | E | F |
|---|---|---|---|---|---|---|
| Location 1 | Saturated $CuSO_4$ | Saturated Ninhydrin (in $CH_3CN$) | Saturated Ninhydrin (in $CH_3CN$) | Saturated Ninhydrin (in $CH_3CN$) | 5 mM TCNQ in $CH_3CN$ | |
| Location 2 (Swipe position) | Saturated $CuSO_4$ | Saturated Ninhydrin (in $CH_3CN$) | Saturated Ninhydrin (in $CH_3CN$) | Saturated Ninhydrin (in $CH_3CN$) | 5 mM TCNQ in $CH_3CN$ | |
| Location 3 | | Saturated Ninhydrin (in $CH_3CN$) | Ampicillin (10 mg/mL) | Amoxicillin (10 mg/mL) | | 2M $Co(SCN)_4$ |
| Location 4 | | Saturated Ninhydrin (in $CH_3CN$) | Saturated Ninhydrin (in $CH_3CN$) | Saturated Ninhydrin (in $CH_3CN$) | | |
| Location 5 | | Saturated Ninhydrin (in $CH_3CN$) | Saturated Ninhydrin (in $CH_3CN$) | Saturated Ninhydrin (in $CH_3CN$) | | |
| Location 6 | Saturated $K_2CO_3$ | Saturated $K_2CO_3$ | Saturated $K_2CO_3$ | Saturated $K_2CO_3$ | Saturated $K_2CO_3$ | |

TABLE 7

Placement of reagents on the β-lactam PAD, lanes G-L. The quantity of each reagent is 4 μL.

| Lane | G | H | I | J | K | L |
|---|---|---|---|---|---|---|
| Location 1 | | | | | 0.1M $BaCl_2$ | Saturated $NiCl_2$ |
| Location 2 (Swipe location) | 2M NaOH | | | | | |
| Location 3 | | 1% $I_3$ (w/v) with 4% Povidone (w/v) | 2M $FeCl_3$/ detergent solution 2:1 (v/v) | 2M $FeCl_3$ | | Saturated Nioxime |
| Location 4 | $NaNO_2$ (30 mg/mL) | | | | 25 mM rhodizonate | |
| Location 5 | Nitroaniline (10 mg/mL in HOTs) | | | | | |
| Location 6 | | | | | | |

TABLE 8-continued

Colors of positive results

| Lane | Analyte | Positive Result Color |
|------|---------|----------------------|
| F | amodiaquine | Green |
|   | chloroquine | Blue |
| G | acetaminophen and amoxicillin | Orange |
| H | starch | Dark blue/black |
| I | carbonate | Orange |
|   | degraded aspirin | Purple |
|   | acetaminophen | Grey |
| J | carbonate | Orange |
|   | degraded aspirin | Purple |
|   | acetaminophen | Grey |
| K | sulfate | Colorless or yellow |
| J | timer | Pink |

Lane A—Testing for β-lactams $CuSO_4$ reacts with β-lactams, such as those present in ampicillin and amoxicillin. When no β-lactam is present, this reagent is sky blue. The reaction with a β-lactam forms a green-colored compound whose chromatographic mobility is slower than the solvent front.

Sensitivity: 100% in lab testing (6/6 true positives); 95.2% in Kenyan field trials (sample size=35)

Specificity: 100% in lab testing (48/48 true negatives); 92.9% in Kenyan field trials (sample size=35)

Lane B—Testing for Ampicillin and Amoxicillin

Ninhydrin reacts with many amines to form colored compounds. In this test, ninhydrin and $K_2CO_3$ react with ampicillin forming an orange color, or with amoxicillin forming a green color.

Sensitivity: 100% in lab testing (correctly identified ampicillin or amoxicillin) of 5/5 true positives; 94.7% in Kenyan field trials (sample size=34)

Specificity: 100% in lab testing of 44/44 true negatives; 100% in Kenyan field trials Lane C—Control Lane for Ampicillin This test contains the same reagents as lane B and also contains ampicillin that has been put on the PAD, giving a positive result, an orange color, even when ampicillin is not present in the pharmaceutical product that is tested. The orange color may become overpowered by green when more than 0.1 mg of amoxicillin from the tablet being analyzed is present in the lane.

Lane D—Control Lane for Amoxicillin

This test contains the same reagents as lane B and also contains amoxicillin. This lane will give a green positive result whether amoxicillin is present in the tested pharmaceutical or not. The green color may be overpowered by orange when more than 0.1 mg ampicillin from the tablet being analyzed is present in the lane.

Lane E—Testing for Reducing Agents

TCNQ is an indicator of strong reducing agents, such as Vitamin C. The analyte reduces the TCNQ, forming a colored compound.

Lane F—Cobalt Complex Test

It is believed that the cobalt forms a colored metal complex with many tertiary amines, such as those found in amodiaquine and chloroquine. The color of the complex varies depending on the analyte. With amodiaquine, the complex is green; with chloroquine, the complex is blue.

Sensitivity=100% in lab testing of 6/6 true positives;
Specificity=100% in lab testing of 47/47 true negatives Lane G—Testing for Acetaminophen and Amoxicillin Nitroani line, when combined with $NaNO_2$ in the presence of acid, forms a diazo group that readily reacts with phenols under basic conditions. The product of the reaction is dark orange. Amoxicillin and acetaminophen both have phenol groups, and give a positive result with this test.

Sensitivity=100% in lab testing of 12/12 true positives.
Specificity=100% in lab testing of 41/41 true negatives.

Lane H—Testing for Starch

Starch is a common binding agent. In some pharmaceutical formulations, it is the expected binder. But many antibiotics do not use starch as the binder such that its presence is a suspicious sign. Some counterfeit formulations may reduce the amount of the active pharmaceutical with flour or other starchy white powders. In this test, starch in the pharmaceutical product being tested reacts with the iodine that is stored on the PAD as an iodine-polyvinylpyrrolidone complex. The starch-iodine complex is dark blue in color, and often so darkly colored that it appears black.

Sensitivity=100% in lab testing of 25/25 true positives; 77.8% in Kenyan field trials (sample size=35)

Specificity=100% in lab testing of 27/27 true negatives; 96.2% in Kenyan field trials Lane I/J—Testing for Carbonate Carbonate is an excipient not expected to be found in authentic antibiotic pharmaceuticals. In this test, iron complexes to the carbonate, forming an orange-colored precipitate that does not elute with water. Complexes with other analytes form different colored compounds. The complex with degraded aspirin (salicylic acid) is purple, while the complex with acetaminophen is grey, and both of these complexes elute up the lane in water.

Lane J also contains detergent while lane I does not. The detergent helps the iron solution to wet hydrophobic powders which may be present in pharmaceutical formulations. The rest of the reaction chemistry can then proceed, as in lane I.

Sensitivity (in testing for carbonate)=50% in lab testing of 3/6 true positives; 90% in Kenyan field trials (sample size=72)

Specificity (in testing for carbonate)=100% in lab testing of 48/48 true negatives; 88.5% in Kenyan field trials Lane K—Testing for Sulfate In this test barium(II) ions are allowed to flow through the deposited pharmaceutical sample. If no sulfate is present, the barium goes up the lane until it reacts with sodium rhodizonate, forming a pink/orange barium rhodizonate complex. If sulfate is present, it traps the barium and prevents formation of the pink color.

Lane L—Timer

The nickel-binding ligand nioxime travels up the lane of the PAD, and forms a complex with nickel to form a pink color. This color will form regardless of the composition of the pharmaceutical being tested, and alerts the user that the PAD has finished running.

Figure 6:
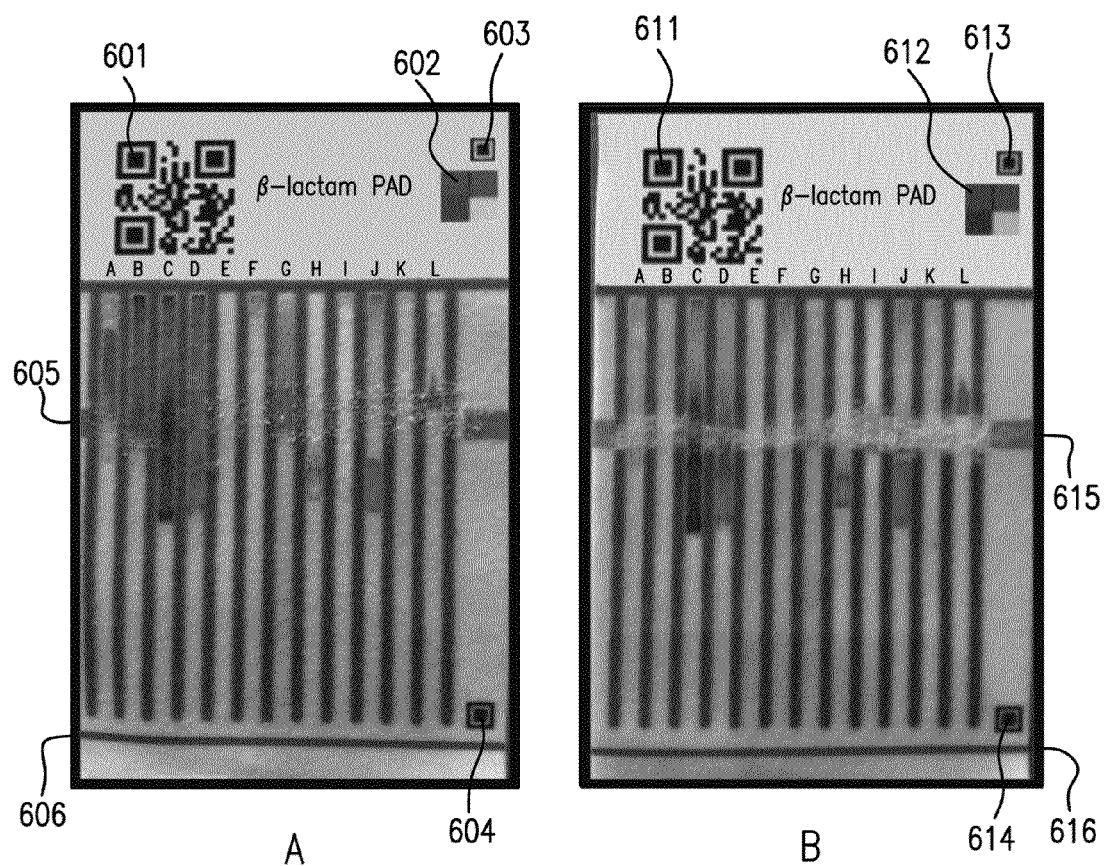
FIGS. 6A and B show the results of testing a genuine antibiotics sample (A) and a chalk (B) with the beta-Lactam PAD.

FIGS. 6A and B show captured images of bate-lactam PADs after reacting with one genuine antibiotics sample (A) and chalk (B). QR codes (601, 611) contain information about the PAD-type, serial number and fabrication date, and allow for remote identification of the PAD. Color calibration zones (602, 612) allows for accurate computer analysis of PAD images taken under varying light conditions. Fiducial markers (603, 613, 604, 614) aid in orienting the captured image so that the image software can correct or transform the captured image. To run the test, the PAD is placed in solvent up to solvent line (605, 615), which allows the antibiotic analyte to interact with reagents and indicators in each of Lanes A-J. The genuine sample (FIG. 6A) shows the expected colors in each of lanes A-L while the chalk sample (FIG. 6B) does not.

Example 6

Paper Analytical Device for Analyzing Erythromycin

Figure 7:
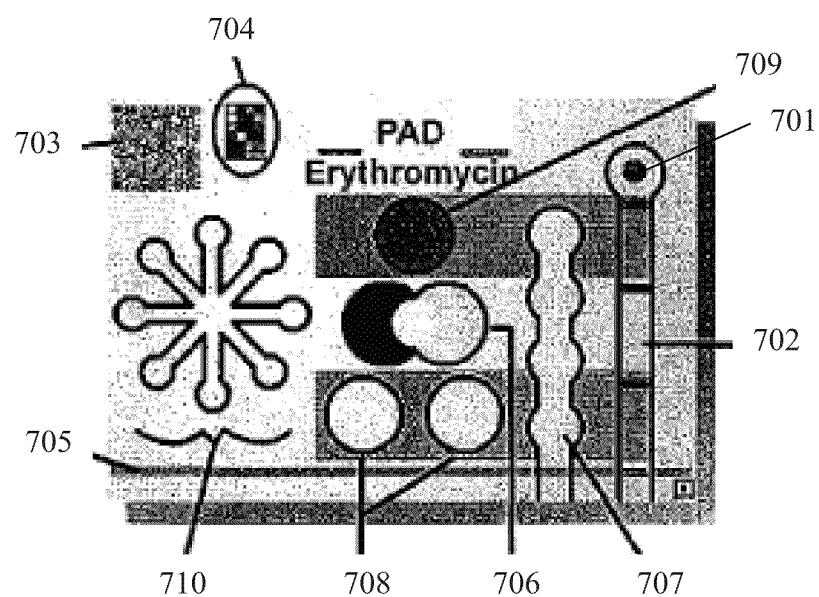
FIG. 7 depicts a erythromycin PAD according to one embodiment.

The erythromycin PAD as shown in FIG. 7 is made with the lanes and dots adhered to a plastic backing. When the dot (701) at the end of the timer lane (702) turns red, the test is complete and it is time for the image to be taken and sent. QR code (703) contains information about the PAD-type, serial number and fabrication date, and allows for remote identification of the PAD. It will even allow the compilation of a database of when, where and what kind of drug counterfeiting occurs around the world wherever erythromycin PADs are used. Color calibration zone (704) allows for accurate computer analysis of PAD images taken under varying light conditions. To run the test, the PAD is placed in solvent up to line (705), which allows the antibiotic analyte to interact with reagents and indicators in each assay regions for cladinose ring tests (706), an alizarin C-concentration ladder test (707), a tertiary amine (Ninhydrin) test (708), a ferric iron macrolide test (708), a cobalt-thiocyanate (CoSCN) test (709), and a Red Flag Wheel contamination test (710). These assay regions are explained in details hereinbelow.

Cladinose Ring Tests (Acid Spot Tests)

The semi quantitative determination of erythromycin (or other similar drugs) by the simultaneous testing with two agents revealing concentration by differential changes and thereby control for effects of higher or lower pH.

Two solutions are created. Indicator solution A is 0.01M HCl and Bromocresol Green pH indicator. Indicator solution B is 0.01M HCl and Methyl Yellow pH indicator. These indicator solutions are impregnated into the PAD surface such that a drop of unknown solution applied between them will interact with both.

The target pH will result in a yellow color in both indicator solutions. A low pH (indicating a too low concentration of erythromycin and/or some relatively acidic contaminant) will cause a blue/green color in the solution A zone (yellow in the solution B zone). A high pH (indicating too great of a concentration of erythromycin and/or some relatively basic contaminant) will cause an orange/red color to develop in the solution B zone (yellow in solution A zone).

When erythromycin solution is applied to the test site, it is denatured and loses the cladinose ring. This results in a change in the pH of the solution.

Alizarin C—Concentration Ladder Test

Alizarin Complexone indicator solution combined with 0.01 M HCl is applied to the PAD surface in consecutive lines along a lane. When erythromycin solution is applied to the drop zone at the end of the lane, capillary action draws it up into each indicator line in succession. If the erythromycin (which is basic) is sufficiently concentrated it will turn all of the lines a dark lilac color. If it is insufficient, the lines will turn a pale peach (approximately pH 7) or remain the yellow of Alizarin C with acid.

Tertiary Amine (Ninhydrin) Test

The Ninhydrin test is commonly used to screen samples for primary and secondary amines but here is catalyzed and used to determine a tertiary amine. Ninhydrin reacts with the amine from erythromycin causing a deep purple/blue color (Ruhemann's Purple) to form in a circle. A lithium acetate buffer of pH 5.2 is used to catalyze the reaction and allows the reaction to take place under 10 minutes. It also prevents oxidation of ninhydrin solution, increasing the stability over time. The PAD is first impregnated with a ninhydrin solution of 1.5% by weight in acetone and allowing it to dry before impregnating it with the buffer. Ruhemann's purple begins forming along the edges in a ring when two molecules of ninhydrin join together by replacing their hydroxyl groups with a nitrogen from the amine.

CoSCN Test

The CoSCN solution is prepared by combining 1 part cobalt salt and 4 parts thiocyanate salt. This solution is a distinct blue color. This is then impregnated into the PAD surface. When erythromycin solution is applied a white color develops due to the presence of the tertiary amine. This color change is visually distinguishable from changes caused by the presence of other amine groups.

Ferric Iron Macrolide Test $FeCl_2$ solution is prepared by combining 0.08 g of $FeCl_2$ with 2 mL each distilled $H_2O$ and concentrated $H_2SO_4$, and then this is diluted to 100 mL with concentrated glacial acetic acid (this may be changed to a saturated $FeCl_2$ solution after further experimentation has been done). When saturated erythromycin solution is applied to this, a dark green blue color develops. This is likely due to the formation of a tetraenylic cation in the macrolide ring in the erythromycin that forms the colored product with the ferric iron. At this time the test takes too long to be feasible for PAD production so a catalyst of some kind will be added.

Contaminant Detection—"Red Flag" Wheel Test

Tests for common counterfeit contaminants such as chalk, starch, vitamin C, acetaminophen, ibuprofen, aspirin, lactose and glucose circle around a central drop zone with a small lane extending to each. Saturated pill solution is applied to the central drop zone and capillary action draws the solution into each reaction zone. If any of these "red flags" reacts with the pill solution it is likely that the pill is of low quality.

Example 7

Devices for Detecting Iodine Levels in Iodized Salt

To prevent iodine deficiency disorders, nearly all countries have a salt iodization program. However, many developing countries lack the resources to monitor properly the iodine content. The iodine is in the forms of iodide or iodate, usually at a level of 20-80 ppm of iodine atoms with respect to NaCl.

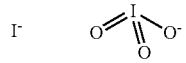

Structure of Iodide and Iodate.

Figure 8:
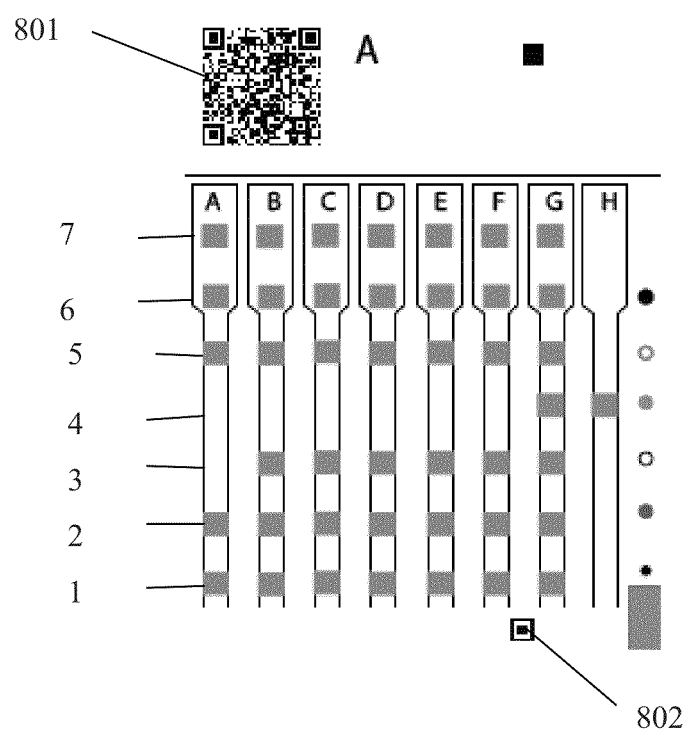
FIG. 8 depicts a salt PAD according to one embodiment.

The salt PAD aims to quantify these compounds. The salt PAD can be adjusted to measure different levels of iodine supplementation, but one possible formulation is given in Table 9 and FIG. 8, including reagent concentration, volume, and deposition location. All spacing of reagents and lanes in this implementation is 9 mm in order to accommodate the use of a solution delivery robot, but other implementations could use spot distances as small as 2 mm and as large as several cm. The numbers indicate the vertical spot locations along the lane, thus spot #1 is at the very bottom of the lane, and spot #2 lies 9 min above it. The number of lanes in this implementation of the PAD is 7, but that number can be increased as well to get different detection levels.

TABLE 9

Possible deposition locations (gray squares) of reagents on salt PAD

| | A | B | C | D | E | F | G |
|---|---|---|---|---|---|---|---|
| 7 | DMG | DMG | DMG | DMG | DMG | DMG | DMG |
| 6 | NiCl2 | NiCl2 | NiCl2 | NiCl2 | NiCl2 | NiCl2 | NiCl2 |
| 5 | Starch | Starch | Starch | Starch | Starch | Starch | Starch |
| 4 | Blank | Blank | Blank | Blank | Blank | Blank | Sat Thio |
| 3 | Blank | 10 mM Thio | 75 mM Thio | $IO_3^-$ | 20 mM Thio | 100 mM Thio | Sat Thio |
| 2 | $NO_2^-$ | $NO_2^-$ | $NO_2^-$ | $I^-$ | $I^-$ | $I^-$ | $I^-$ |
| 1 | HOTs | HOTs | HOTs | HOTs | HOTs | HOTs | HOTs |

All volumes = 2.0 uL
[$I^-$] = 40 mM
[$IO_3^-$] = 5 mM
[$NO_2$] = 100 mM
HOTs = Tosic acid = 500 mM
DMG = Dimethylglyoxime = 100 mM
[NiCl2] = 200 mM
Starch = 2%
Thio = thiosulfate

TABLE 10

Capability of each lane to detect the levels of analytes, with a blue color in each lane corresponds to the levels of analytes indicated.

| A | B | C | D | E | F | G |
|---|---|---|---|---|---|---|
| 30 ppm Iodide | 50 ppm Iodide | 210 ppm Iodide | Positive Control | 5 ppm Iodate | 20 ppm Iodate | 40 ppm Iodate |

Lanes A, B, and C

These lanes follow the chemical reactions shown in Scheme 1. The levels of thiosulfate vary in each lane to allow determination of a target quantity of iodide. Thiosulfate levels required to detect specific quantities of iodide are NOT stoichiometric, as would be expected by one skilled in the art of analytical chemistry, due to the particular flow dynamics of the paper tests.

Scheme 1. Reactions used to detect iodide.

$$4H^+ + 3I^- + 2NO_2^- \leftrightarrow I_3^- + 2H_2O + 2NO$$
$$I_3^- + 2S_2O_3^{2-} \leftrightarrow 3I^- + S_4O_6^{2-}$$
$$I_3^- + Starch \leftrightarrow Blue\ Complex$$

Iodide travels up each lane from the salt test solution, is oxidized to triiodide, and then is reduced back to iodide by thiosulfate. When too little thiosulfate is present in the lane, triiodide will exist, and the lane will turn blue from the triiodide-starch complex.

Sensitivity for detection of iodide was 73% (n=59), while specificity was 100% (n=70), according to a field test by student volunteers at the University of Notre Dame in the spring of 2012.

Lane D

This lane follows the chemical reactions shown in Scheme 2. Lane D is used as a positive control, meaning a blue response will always appear demonstrating reagent stability and proper fabrication of the PAD.

Scheme 2. Reactions used for a positive control.

$$6H^+ + IO_3^- + 8I^- \leftrightarrow 3I_3^- + 3H_2O$$
$$I_3^- + Starch \leftrightarrow Blue\ Complex$$

Sensitivity: 92% (n=160) was recorded in a field test study at the University of Notre Dame in the spring of 2012.

Lanes E, F, G

These lanes follow the chemical reactions shown in Scheme 3. The levels of thiosulfate vary in each lane to allow determination of a certain quantity of iodate. Thiosulfate levels required to detect specific quantities of iodide are NOT stoichiometric, as would be expected by one skilled in the art of analytical chemistry, due to the particular flow dynamics of the paper tests.

Scheme 3. Reactions used to detect iodate.

$$6H^+ + IO_3^- + 8I^- \leftrightarrow 3I_3^- + 3H_2O$$
$$I_3^- + 2S_2O_3^{2-} \leftrightarrow 3I^- + S_4O_6^{2-}$$
$$I_3^- + Starch \leftrightarrow Blue\ Complex$$

Iodate travels up the lane from the salt test solution, is reduced to triiodide, and then reduced further to iodide by thiosulfate. When too little thiosulfate is present in the lane, triiodide will exist, and the lane will turn blue from the triiodide-starch complex.

Sensitivity for detection of iodate was measured as 100% (n=53) and specificity as 97% (n=76) in a field test study at the University of Notre Dame in the spring of 2012.

All Lanes

Each lane contains an indicator at the top to signal the test is done running. The reaction is shown in Scheme 4.

Scheme 4. Reaction used as stop indicator.

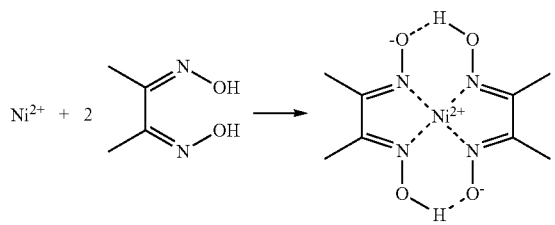

All reactions in Scheme 1-4 have been carried out only under room temperature and humidity. The stability of the reagents on the PAD is not known, but suspected to be days, possibly months as one PAD ran correctly after 2 months.

Another important part of the salt PAD is an optional lane to detect diethylcarbamazine citrate (DEC). In an attempt to eradicate the parasitic disease lymphatic filariasis in Haiti, the Haiti Program at the University of Notre Dame is also fortifying salt with diethylcarbamazine citrate (DEC). DEC is an antiparasitic drug that is used to treat lymphatic filariasis. The salt PAD contains a test that is able to detect DEC in salt. The therapeutic range for DEC and the target for fortification in the salt is 0.2%-0.6% DEC by weight. By incorporating this lane onto the salt PAD, quality control for salt that is iodized and supplemented with DEC can be carried out in a single inexpensive and fast test. The structure of DEC is shown below:

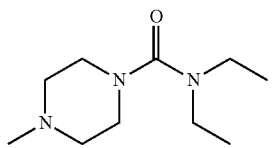

DEC structure (excluding citric acid present as counterion in the drug)

Table 11 herein shows the location of the embedded reagents, the amounts embedded, the chemicals to be detected, the color change expected with a positive reaction, and the minimum amount of the chemical or active agent necessary in order to result in a positive reaction. The following is a description of the various regions of the PAD, their content and how they are used to analyze a particular sample of salt.

TABLE 11

Various regions of the salt PAD, their content and how they are used to analyze a particular sample of salt.

| Lane | Reagent (μL) | Detects | Color | Minimum Threshold for Positive Reaction |
|---|---|---|---|---|
| H | Bromothymol Blue: 5 mM (4 μL) | Diethyl-carbamazine citrate (DEC) | Negative: blue to light purple color Positive for DEC: yellow green color | ~13 g salt/ 20 mL water (saturated NaCl) with ~3.3 mM DEC |

Bromothymol blue forms an ion pair with diethylcarbamazine citrate. The indicator by itself is a blue to light purple color. When an ion pair forms with DEC, the indicator changes to a yellow green color. It is important that the solutions used are neutral since bromothymol blue is a pH indicator. A buffer such as pH 7 phosphate may be added to lane H to ensure neutrality of the analysis solution.

Under the fabrication and running conditions described above, bromothymol blue changes color in the presence of at least 3 mM DEC. The lowest therapeutic level of DEC loading of the salt (0.2% w/w) should produce an analysis solution with a 5.1 mM DEC concentration under the running conditions described above.

Samples tested include the following:
Samples that gave the expected color change: Haitian salt with 0.2% DEC (iodized to 80 ppm) mixed 1:1 with DI water, saturated NaCl solution with DEC present at 100 mM, 20 mM, 10 mM, 9 mM, 8 mM, 7 mM, 6 mM, 5 mM, 4 mM, 3.3 mM, 3 mM;
Samples that did not give color changes: DI water, hot tap water, Haitian salt without DEC, Celtic Sea Salt, Morton's Sea Salt, GFS Iodized Salt, saturated NaCl solution with DEC present at 2 mM, 1 mM, and 0.1 mM.

Example 8

Automatic Analysis of Pad Images by Transformation Using QR Code and Finder Markers Firstly, using a mobile camera device to capture an image of a PAD after the tests on the PAD have been performed. Three types of PADs, namely, acetaminophen PAD, salt/DEC PAD and TAM IFLU® PAD are used. Although the PAD may be rotated in the camera's field, it must be in focus when the image is taken. To increase the chances of producing a good input image, a method of taking a picture from a standard distance is developed as follows. Specifically, after performing the tests, the PAD is placed next to a plastic cup of standard height and the mobile camera device is placed on top of the plastic cup to take a picture of the PAD. This method produces a straight picture of the PAD with little angle either towards or away from the PAD.

Figure 9:
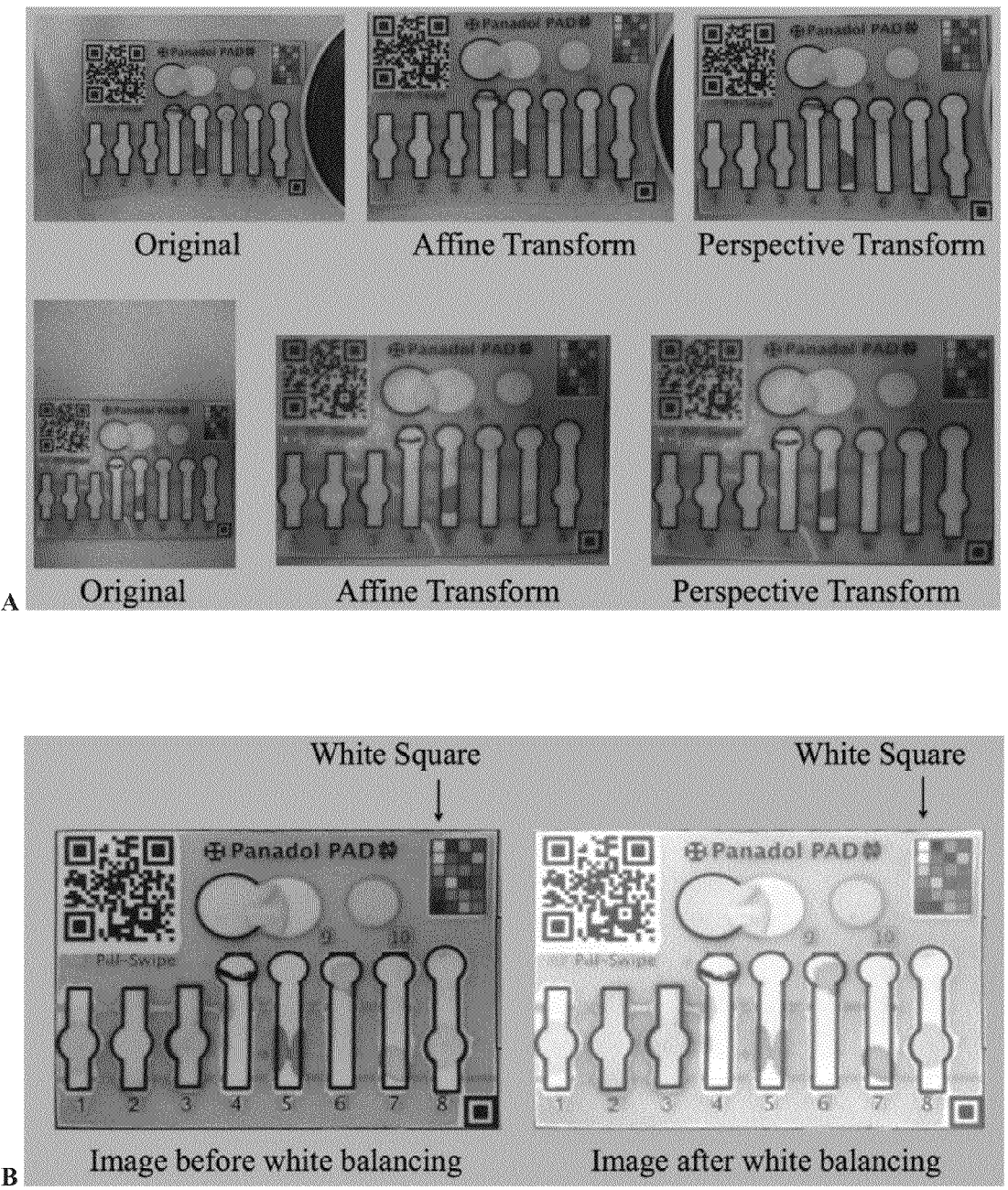
FIGS. 9A and B depict transformation or correction (A) and white correction (B) of PAD images.

Secondly, the finder marks in the image are detected and located using the open-source ZXing package, and the finder mark locations are used to transform the image to the canonical coordinate system to correct perspective distortions. As shown in FIG. 9A, two types of transformations can be performed. One is the affine transformation, which uses the positions of the three finder marks in the QR code, while the other is the perspective transformation, which uses the positions of the three finder marks in the QR code, together with the position of the finder mark in the opposite corner as the QR code. The data show that the perspective distortion model for image transformation is more general and its use for the distortion correction is preferred over the affine distortion model provided that a fourth point is available to enable its use.

Thirdly, as shown in FIG. 9B, the image's white balance is corrected.

Lastly, the color changes of the PAD regions of interest are identified to determine a qualitative or qualitative test result. While the precise amount of active agent may not be identified, the brightness or intensity of the assaying region can provide some indication of the relative amount of active agent that is present in the product tested.

The various embodiments described above are provided by way of illustration only and should not be construed to limit the invention. Those skilled in the art will readily recognize the various modifications and changes which may be made to the present invention without strictly following the exemplary embodiments illustrated and described herein, and without departing from the true spirit and scope of the present invention, which is set forth in the following claims.

What is claimed is:

1. A paper analytical device for detection of at least two chemical components indicative of a low quality pharmaceutical product, comprising:
   a porous, hydrophilic medium;
   at least two assay regions associated with the porous, hydrophilic medium;

at least one assay reagent or precursor thereof in a portion of each of the at least two assay regions;
at least one sample deposition area present on the device which extends across the medium and intersects each of the at least two assay regions and which indicates where a pharmaceutical product may be disposed upon the medium for contact with assay reagents or precursors in the assay regions by capillary transport when the device receives solvent for activation; and
at least one optically readable information zone which after activation of the device provides color information necessary for detection of the at least two chemical components,
wherein the at least two assay regions and at least one sample deposition area are arranged on the device to allow, after activation of the device, capillary flow of (a) the pharmaceutical product from the deposition area to the portions of the assay regions that contains the reagents or precursors, or (b) the reagents or precursors from the portions of the assay regions to the pharmaceutical product in the deposition area;
wherein the at least one optically readable information zone comprises alignment references for transforming or correcting a captured image of the paper analytical device to facilitate analysis, and wherein the device further includes a color calibration zone that includes reference colors to assist in processing of the color information obtained from the assay regions after activation of the device to more accurately detect the at least two chemical components.

2. The device of claim 1, wherein the alignment references include a plurality of fiducial markers for orienting the captured image, and the device further includes an identification tag of a two-dimensional barcode.

3. The device of claim 1, further comprising a hydrophobic barrier or an air gap that is present to define multiple assay regions with multiple assay reagents or precursors thereof arranged in a defined pattern to facilitate contact with the chemical components to be tested, and a solvent contact zone that contacts a lower portion of each assay region and that provides an indication of how the device should be placed in a solvent reservoir so that the solvent can activate the device by travel through the assay regions by capillary action.

4. The device of claim 1, further comprising user compliance regions that include a timer region that indicates when the test is completed.

5. The device of claim 1, wherein the chemical components to be detected include an active ingredient and an excipient wherein the active ingredient includes an anti-malarial, antibiotic, anti-parasitic, cox-inhibitor, analgesic, antipyretic or anti-viral compound and wherein the color information determines whether an inappropriate combination of active ingredient and excipient is present, indicative of a low quality pharmaceutical product.

6. A method for detection of at least two chemical components indicative of a low quality pharmaceutical product, which comprises:
providing an analytical device according to claim 1;
disposing the pharmaceutical product to be analyzed on the medium in the at least one deposition area;
activating the device by contact with a solvent to allow (a) the pharmaceutical product to flow by capillary action from the deposition area to the portions of the assay regions that contains the reagents or precursors, or (b) the reagents or precursors to flow by capillary action from the portions of the assay regions to the pharmaceutical product in the deposition area, so that the assay reagents or precursors and the pharmaceutical product come into contact to interact to provide color information for analysis; and
analyzing the color information to detect the presence or absence of the at least two chemical components;
wherein the disposing of the pharmaceutical product on the medium includes (a) rubbing a tablet, pill or other solid pharmaceutical product across or along the deposition area, (b) opening a capsule of a pharmaceutical product and spreading capsule contents along the deposition area, (c) applying a powder of a pharmaceutical product along the deposition area, or (d) applying a liquid pharmaceutical product along the deposition area.

7. The method of claim 6, wherein disposing the pharmaceutical product into the assay regions and activating the device cause a color change that can be analyzed to detect the presence or absence of the chemical components in the pharmaceutical product.

8. The method of claim 6, which further comprises automating the color analysis by:
capturing an image of the device using a camera device; and
providing image analysis software capable of recognizing and quantifying a color change within the assay regions of the device that is shown in the captured image compared to the colors of the color calibration zone.

9. The method of claim 8, wherein the device includes a plurality of fiducial markers for orienting the captured image, and wherein the image software corrects or transforms the captured image based on the fiducial marks, thereby aligning the captured image with stored images in the database, reads test results from pre-specified regions in transformed image, and classifies the test results.

10. The method of claim 9, which further comprises providing the image analysis software on the camera device for processing the captured image in situ, or on a network server wherein the captured image is processed by sending the image to the network server that performs the analysis and transmitting detection results back to the camera device.

11. The method of claim 8, which further comprises repeating the detection for a plurality of pharmaceutical products: and compiling a database of the captured images of the analytical devices, including time stamping and geo-tagging of the captured images.

12. A method for identifying geographical areas or points in time that low quality pharmaceutical products are being provided, which comprises:
collecting images of color information and compiling a database of the captured images of the analytical devices, including time stamping and geo-tagging of the captured images according to the method of claim 11; and
processing the database to identify locations or times that a plurality of low quality pharmaceutical products are being provided.

13. The method of claim 12, which further comprises collecting an image from analysis of a further pharmaceutical product, and comparing results to the images in the database to identify locations where identical low quality pharmaceutical products are being provided.

14. The method of claim 6, wherein the chemical components to be detected include an active ingredient and an excipient, and:
the presence of one of the chemical components determines that the pharmaceutical product contains an insufficient amount of active ingredient;

the absence of one of the chemical components determines that the pharmaceutical product does not contain an appropriate active ingredient;

the absence of one of the chemical components determines that the pharmaceutical product does not contain an appropriate excipient; or the presence of one of the chemical components determines that the pharmaceutical product contains an inappropriate excipient.

15. The method of claim 14, wherein the chemical components to be detected include an active ingredient and an excipient, wherein the active ingredient includes an anti-malarial, antibiotic, anti-parasitic, cox-inhibitor, analgesic, anti-pyretic or anti-viral compound and wherein the color information determines whether an inappropriate combination of active ingredient and excipient is present, indicative of a low quality pharmaceutical product.

16. A kit for detection of at least two chemical components indicative of a low quality pharmaceutical product, the kit comprising:

an analytical device according to claim 1; and instructions for using the kit, wherein the instructions include instructions for disposing of the pharmaceutical product on the medium by (a) rubbing a tablet, pill or other solid pharmaceutical product across or along the deposition area, (b) opening a capsule of a pharmaceutical product and spreading capsule contents along the deposition area, (c) applying a powder of a pharmaceutical product along the deposition area, or (d) applying a liquid pharmaceutical product along the deposition area, and instructions for activating the device for detecting the presence or absence of the at least two chemical components indicative of a low quality pharmaceutical product using the kit, or a link to retrieve the instructions from a website.

17. The kit of claim 16, wherein the device includes solvent contact zone that contacts a lower portion of each assay region and that provides an indication of how the device should be placed in a solvent reservoir so that the solvent can travel through the assay regions by capillary action; and further comprising a solvent that is present in an amount sufficient to dilute the pharmaceutical product to be analyzed to an analyzable concentration.

18. A paper analytical device for analyzing the quality of a pharmaceutical or food product, comprising:

a porous, hydrophilic medium;

at least two elongated assay regions associated with the porous, hydrophilic medium;

at least one assay reagent or precursor thereof in each of the at least two assay regions, wherein the at least one assay reagent or precursor is capable of identifying a component of the pharmaceutical or food product, and is present at different concentrations in each of the at least two assay regions to facilitate quantitative analysis of said component, at least one sample deposition area present on the device which extends across the medium and intersects each of the at least two assay regions and which indicates where a pharmaceutical product may be disposed upon the medium for contact with assay reagents or precursors in the assay regions; and at least one optically readable information zone which after activation of the device provides color information necessary for quantitative analysis of said component, and a color calibration zone, wherein the at least two assay regions and at least one sample deposition area are arranged on the device so that the deposition area is located perpendicular to the at least two elongated assay regions to allow, after activation of the device, capillary flow of (a) the pharmaceutical product from the deposition area to the portions of the assay regions that contains the reagents or precursors, or (b) the reagents or precursors from the portions of the assay regions to the pharmaceutical product in the deposition area;

wherein the least one optically readable information zone comprises alignment references for transforming or correcting a captured image of the paper analytical device to facilitate analysis, and wherein the color calibration zone that includes reference colors to assist in processing of the color information obtained from the assay regions after activation of the device to more accurately detect the quantity of said component in the pharmaceutical or food product.

19. The device of claim 18, wherein the at least two elongated assay regions are oriented in lanes in one direction on the hydrophilic medium, a timer region that indicates when the test is completed is provided on the hydrophilic medium and is oriented in a lane in the same direction as and in alignment with the assay regions, and the at least one deposition area is located perpendicular to the lanes of the assay and timer regions, with each lane separated by a hydrophobic barrier or an air gap and the assay reagents or precursors in each lane of the assay regions being located above, below or at a deposition area so that disposing of the pharmaceutical product along the deposition area and the assay and timer regions with activation of the device cause a color change that can be analyzed to detect the presence or absence of the chemical components in the pharmaceutical product.

20. The device of claim 19, further comprising contact zone that contacts a lower portion of each assay region and that provides an indication of how the device should be placed in a solvent reservoir, wherein at least 8 to 12 lanes are provided, including control regions comprising the timer region and one or both of a positive or negative control region, each control region oriented in a lane in the same direction as and in alignment with the other lanes, and wherein each lane is configured and arranged to allow the lanes to be filled with the solvent by capillary action from the solvent reservoir.

* * * * *